United States Patent
Habash

(10) Patent No.: US 11,510,913 B1
(45) Date of Patent: Nov. 29, 2022

(54) MODULATING EXPRESSION LEVEL OF A GENE ENCODING AN APURINIC/APYRIMIDINIC ENDODEOXYRIBONUCLEASE PROTEIN BY TREATING A HUMAN SUBJECT WITH A NITROXIDE

(71) Applicant: Louis Habash, Irvine, CA (US)

(72) Inventor: Louis Habash, Irvine, CA (US)

(*) Notice: Subject to any disclaimer, the term of this patent is extended or adjusted under 35 U.S.C. 154(b) by 0 days.

(21) Appl. No.: 17/330,182

(22) Filed: May 25, 2021

(51) Int. Cl.
| | |
|---|---|
| *A61K 31/445* | (2006.01) |
| *A61P 35/00* | (2006.01) |
| *A61P 9/10* | (2006.01) |
| *A61P 31/00* | (2006.01) |
| *A61P 25/00* | (2006.01) |

(52) U.S. Cl.
CPC .............. *A61K 31/445* (2013.01); *A61P 9/10* (2018.01); *A61P 25/00* (2018.01); *A61P 31/00* (2018.01); *A61P 35/00* (2018.01)

(58) Field of Classification Search
CPC .................................................. A61K 31/445
See application file for complete search history.

(56) References Cited

U.S. PATENT DOCUMENTS

| | | |
|---|---|---|
| 5,352,442 A | 10/1994 | Proctor |
| 5,462,956 A | 10/1995 | Mitchell et al. |
| 11,324,737 B1 | 5/2022 | Habash |
| 2009/0042937 A1 | 2/2009 | Habash et al. |
| 2010/0179188 A1 | 7/2010 | Rouault et al. |
| 2012/0046314 A1 | 2/2012 | Habash et al. |
| 2019/0224178 A1 | 7/2019 | Habash |

FOREIGN PATENT DOCUMENTS

WO    WO 2002/026231 A1    4/2002

OTHER PUBLICATIONS

Karmeli et al. ("Astable nitroxide radical effectively decreases mucosal damage in experimental colitis," Gut, 1995, 37, 386-393).*
Grundy, et al. "Base excision repair and its implications to cancer therapy". Essays Biochem Oct. 26, 2020; 64 (5): 831-843. doi: https://doi.org/10.1042/EBC20200013).
Poletto, et al. "Inhibitors of the apurinic/apyrimidinic endonuclease 1 (APE1)/nucleophosmin (NPM1) interaction that display antitumor properties." Molecular carcinogenesis vol. 55,5 (2016): 688-704. doi:10.1002/mc.22313.
Fishel, et al. "Apurinic/apyrimidinic endonuclease/redox factor-1 (APE1/Ref-1) redox function negatively regulates NRF2." The Journal of biological chemistry vol. 290,5 (2015): 3057-68. doi:10.1074/jbc.M114.621995.
Reed, et al. "Small-molecule inhibitors of proteins involved in base excision repair potentiate the anti-tumorigenic effect of existing chemotherapeutics and irradiation." Future oncology (London, England) vol. 5,5 (2009): 713-26. doi:10.2217/fon.09.31.
Codrich, et al. "Inhibition of APE1-endonuclease activity affects cell metabolism in colon cancer cells via a p53-dependent pathway." DNA repair vol. 82 (2019): 102675. doi:10.1016/j.dnarep.2019.102675.
Pasha, et al. "Ref-1/APE1 Inhibition with Novel Small Molecules Blocks Ocular Neovascularization". Journal of Pharmacology and Experimental Therapeutics Oct. 2018, 367 (1) 108-118; DOI: https://doi.org/10.1124/jpet.118.248088.
Soule, et al. "The chemistry and biology of nitroxide compounds." Free radical biology & medicine vol. 42,11 (2007): 1632-50. doi:10.1016/j.freeradbiomed.2007.02.030.
Kim et al. Colon cancer progression is driven by APEX1-mediated upregulation of Jagged, J. Clin. Invest., Aug. 2013, vol. 123(8), pp. 3211-3230.
International Search Report and Written Opinion in PCT/US2002/030964 dated Sep. 7, 2022.

* cited by examiner

*Primary Examiner* — Yong S. Chong
(74) *Attorney, Agent, or Firm* — Knobbe, Martens, Olson & Bear LLP

(57) ABSTRACT

Some embodiments disclosed herein include a method for decreasing an expression level of a gene. The methods can include identifying a human subject having an increased expression level of APEX1; and administering to the human subject an effective amount of a nitroxide antioxidant, whereby expression level of the gene is decreased.

11 Claims, No Drawings

MODULATING EXPRESSION LEVEL OF A GENE ENCODING AN APURINIC/APYRIMIDINIC ENDODEOXYRIBONUCLEASE PROTEIN BY TREATING A HUMAN SUBJECT WITH A NITROXIDE

BACKGROUND

Field

The present disclosure relates generally to the field of modulation of gene expression and more particularly to decreasing expression levels of one or more genes relating to endodeoxyribonuclease 1 by treating human subjects with a nitroxide.

Description of the Related Art

Diseases and conditions are treatable by adjusting the expression levels and activities of key genes in the body. Gene expression irregularities, whether overexpressed, activated, under expressed or inhibited underlie the development and progression of every disease and condition. Some diseases are characterized by deficient expression of certain genes while other diseases result from over expression of certain genes. A disease resulting from irregular gene expression can be prevented, treated, or reversed by administering a nitroxide antioxidant to target and correct the expression levels of the genes.

Expression levels of genes are often naturally controlled in an appropriate way, but sometimes natural control of gene expression fails. For example, in cancer, genes providing instructions for cell growth are activated or switched on, when they should be off. Autoimmune diseases and aging are other examples of diseases and conditions that result from irregular gene expression. As cells age, the natural control of gene expression deteriorates promoting several diseases and conditions such as inflammation, chronic pain, infections, neurodegenerative disease, neurological disorders, skin diseases, etc. It is essential to identify the irregular expression of the genes involved in the cause of the disease and adjust the expression levels of those genes.

Often referred to as gene therapy, the targeting and correction of cellular dysfunction through adjusting the expression level of certain genes is necessary to prevent, treat, or reverse a disease or condition. Only by identifying key genes and developing therapeutics that altering the expression patterns of those genes can we prevent the development of the disease, reduce its effects once it has occurred, or reverse it all together.

One of the key genes involved in several diseases and conditions is apurinic/apyrimidinic endodeoxyribonuclease 1 (APEX1). When this gene is overexpressed it causes several diseases and conditions associated with the overexpression of the gene. Thus, correction of the overexpression of APEX1 genes is essential for treatment and prevention of the associated diseases and conditions.

SUMMARY

Some embodiments disclosed herein provide methods for decreasing gene expression. The methods, in some embodiments, include identifying a human subject over the age of 35 and having an increased expression level of APEX1; and administering to the human subject an effective amount of a nitroxide antioxidant resulting in a decreased expression level of the gene. In some embodiments, the gene is APEX1. In some embodiments, the human subject is over the age of 45. In some embodiments, the human subject is over the age of 55. In some embodiments, the human subject is over the age of 65. In some embodiments, the expression level of the gene in a skin tissue is decreased by treatment. In some embodiments, the expression level of the gene in an adipose tissue is decreased by treatment. In some embodiments, the expression level of the gene in blood is decreased by treatment. In some embodiments, the expression level of the gene in a neuronal tissue is decreased by treatment. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods for increasing the expression level of a gene in a human subject in need thereof, comprising: identifying a human subject having an increased expression level of APEX1; administering to the human subject an effective amount of a nitroxide antioxidant, whereby the expression level of APEX1 is decreased. In some embodiments, the gene is APEX1. In some embodiments, the decreased expression level of the gene is age-related. In some embodiments, the human subject is over the age of 35. In some embodiments, the human subject is over the age of 45. In some embodiments, the human subject is over the age of 55. In some embodiments, the human subject is over the age of 65. In some embodiments, the decreased expression level of the gene is disease-related. In some embodiments, the disease is selected from the group consisting of cancer, rheumatoid/osteoid arthritis, systemic lupus erythematosus (SLE), inflammatory bowel disease, Alzheimer's disease, multiple sclerosis, atherosclerosis, cardiovascular disease, cataracts, dementia, osteoporosis, type 2 diabetes, and hypertension. In some embodiments, the disease is age-related. In some embodiments, the expression level of the gene in a skin tissue is decreased by treatment. In some embodiments, the expression level of the gene in an adipose tissue is decreased by treatment. In some embodiments, the expression level of the gene in blood is decreased by treatment. In some embodiments, the expression level of the gene in a neuronal tissue is decreased by treatment. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods for reducing risk of a disease in a human subject in need thereof, comprising: identifying a human subject over the age of 35 having an increased risk of a disease due to an increased expression level of APEX1; administering to the human subject an effective amount of a nitroxide antioxidant, whereby the expression level of APEX1 is decreased. In some embodiments, the disease is selected from the group consisting of cancer, rheumatoid/osteoid arthritis, systemic lupus erythematosus (SLE), inflammatory bowel disease, Alzheimer's disease, multiple sclerosis, atherosclerosis, cardiovascular disease, cataracts, dementia, osteoporosis, type 2 diabetes, and hypertension. In some embodiments, the gene is APEX1. In some embodiments, the human subject is over the age of 45. In some embodiments, the human subject is over the age of 55. In some embodiments, the human subject is over the age of 65. In some embodiments, the expression level of the gene in a skin tissue is decreased by treatment. In some embodiments, the expression level of the gene in an adipose tissue is decreased by treatment. In some embodiments, the expression level of the gene in blood is decreased by treatment. In some embodiments, the expression level of the gene in a neuronal tissue is decreased by treatment. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods comprising: identifying a human subject having or at risk of developing a cancer and in need of a decreased expression level of a APEX1 gene; administering to the human subject an effective amount of a nitroxide antioxidant, whereby the expression level of the gene associated with apurinic/apyrimidinic endodeoxyribonuclease proteins and base excision repair activity is decreased. In some embodiments, the cancer can be selected from the group consisting of bladder cancer, colorectal cancer, hepatocellular carcinoma, prostate carcinoma, and kidney carcinoma. In some embodiments, the gene is APEX1. In some embodiments, the cancer is age-related. In some embodiments, the human subject is over the age of 35. In some embodiments, the human subject is over the age of 45. In some embodiments, the human subject is over the age of 55. In some embodiments, the human subject is over the age of 65. In some embodiments, the expression level of the gene in a skin tissue is decreased by treatment. In some embodiments, the expression level of the gene in an adipose tissue is decreased by treatment. In some embodiments, the expression level of the gene in blood is decreased by treatment. In some embodiments, the expression level of the gene in a neuronal tissue is decreased by treatment. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods comprising: identifying a human subject having or at risk of developing an autoimmune disease and in need of a decreased expression level of a APEX1 gene; administering to the human subject an effective amount of a nitroxide antioxidant, wherein the expression level of the gene associated with apurinic/apyrimidinic endodeoxyribonuclease proteins and base excision repair activity is decreased. In some embodiments, the autoimmune disease can be selected from the group consisting of rheumatoid/osteoid arthritis, systemic lupus erythematosus (SLE), inflammatory bowel disease, multiple sclerosis, atherosclerosis, and osteoporosis. In some embodiments, the gene is APEX1. In some embodiments, the autoimmune disease is age-related. In some embodiments, the human subject is over the age of 35. In some embodiments, the human subject is over the age of 45. In some embodiments, the human subject is over the age of 55. In some embodiments, the human subject is over the age of 65. In some embodiments, the expression level of the gene in a skin tissue is decreased by treatment. In some embodiments, the expression level of the gene in an adipose tissue is decreased by treatment. In some embodiments, the expression level of the gene in blood is decreased by treatment. In some embodiments, the expression level of the gene in a neuronal tissue is decreased by treatment. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods for a disease associated with a decreased expression level of apurinic/apyrimidinic endodeoxyribonuclease proteins and base excision repair activity is decreased in a patient in need thereof, comprising: identifying a human subject having or at risk of developing a disease associated with an increased expression of APEX1; administering to the human subject an effective amount of a nitroxide antioxidant, whereby the expression level of APEX1 is decreased. In some embodiments, the disease can be selected from the group consisting of cancer, rheumatoid/osteoid arthritis, systemic lupus erythematosus (SLE), inflammatory bowel disease, Alzheimer's disease, multiple sclerosis, atherosclerosis, cardiovascular disease, cataracts, dementia, osteoporosis, type 2 diabetes, and hypertension. In some embodiments, the gene is APEX1. In some embodiments, the human subject is over the age of 35. In some embodiments, the human subject is over the age of 45. In some embodiments, the human subject is over the age of 55. In some embodiments, the human subject is over the age of 65. In some embodiments, the expression level of the gene in a skin tissue is decreased by treatment. In some embodiments, the expression level of the gene in an adipose tissue is decreased by treatment. In some embodiments, the expression level of the gene in blood is decreased by treatment. In some embodiments, the expression level of the gene in a neuronal tissue is decreased by treatment. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods for treating an individual in need thereof, comprising: identifying an individual over the age of 35 in need of a decreased expression level of APEX1; and administering to the individual an effective amount of a nitroxide antioxidant to increase the level of expression of the gene associated with apurinic/apyrimidinic endodeoxyribonuclease proteins and base excision repair activity. In some embodiments, the gene is APEX1. In some embodiments, the human subject is over the age of 45. In some embodiments, the human subject is over the age of 55. In some embodiments, the human subject is over the age of 65. In some embodiments, the human subject has an increased expression level of the gene. In some embodiments, the individual has or is at risk of developing an age-related condition. In some embodiments, the age-related condition comprises decreased senescence in a tissue. In some embodiments, the age-related condition comprises inhibition apurinic/apyrimidinic endodeoxyribonuclease proteins and base excision repair activity in a tissue. In some embodiments, the age-related condition comprises decreased molecular heterogeneity. In some embodiments, the age-related condition comprises decreased functional impairment in a tissue. In some embodiments, the expression level of the gene in a skin tissue is decreased by treatment. In some embodiments, the expression level of the gene in an adipose tissue is decreased by treatment. In some embodiments, the expression level of the gene in blood is decreased by treatment. In some embodiments, the expression level of the gene in a neuronal tissue is decreased by treatment. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods for treating an individual in need thereof, comprising: identifying an individual having a disease-related increased expression level of APEX1; and administering to the individual an effective amount of a nitroxide antioxidant to increase the level of expression of the gene associated with apurinic/apyrimidinic endodeoxyribonuclease proteins and base excision repair activity. In some embodiments, the disease can be selected from the group consisting of cancer, rheumatoid/osteoid arthritis, systemic lupus erythematosus (SLE), inflammatory bowel disease, Alzheimer's disease, multiple sclerosis, atherosclerosis, cardiovascular disease, cataracts, dementia, osteoporosis, type 2 diabetes, and hypertension. In some embodiments, the gene is APEX1. In some embodiments, the human subject is over the age of 35. In some embodiments, the human subject is over the age of 45. In some embodiments, the human subject is over the age of 55. In some embodiments, the human subject is over the age of 65. In some embodiments, the expression level of the gene in a skin tissue is decreased by treatment. In some embodiments, the expression level of the gene in an adipose tissue is decreased by treatment. In some embodiments, the expression level of the gene in blood is decreased by treatment. In some embodiments, the expression level of the gene in a neuronal tissue is decreased by treatment. In some embodiments, the nitroxide antioxidant is 4-hydroxy-2,2,6,6-tetramethylpiperidine-1-oxyl. In some embodiments, the effective amount of the nitroxide antioxidant is within a range of 0.01-300 mg/kg. In some embodiments, the effective amount of the nitroxide antioxidant is within a range of 0.1-250 mg/kg. In some embodiments, the effective amount of the nitroxide antioxidant is within a range of 1-200 mg/kg. In some embodiments, the effective amount of the nitroxide antioxidant is within a range of 2-150 mg/kg. In some embodiments, the effective amount of the nitroxide antioxidant is within a range of 5-125 mg/kg. In some embodiments, the effective amount of the nitroxide antioxidant is within a range of 7-100 mg/kg. In some embodiments, the effective amount of the nitroxide antioxidant is within a range of 10-75 mg/kg. In some embodiments, the effective amount of the nitroxide antioxidant is within a range of 15-30 mg/kg.

Some embodiments disclosed herein provide methods for treating an individual having or at risk of developing a condition due to aging, comprising: identifying an individual over the age of 35; and administering to the individual an effective amount of a nitroxide antioxidant, whereby the expression level of the gene associated with apurinic/apyrimidinic endodeoxyribonuclease proteins and base excision repair activity is decreased. In some embodiments, the individual has an increased expression level of the gene. In some embodiments, the gene is APEX1. In some embodiments, the condition is an age-related condition. In some embodiments, the age-related condition comprises increased senescence in a tissue. In some embodiments, the age-related condition comprises underactivation of APEX1 in a tissue. In some embodiments, the age-related condition comprises increased molecular heterogeneity. In some embodiments, the age-related condition comprises increased functional impairment in a tissue. In some embodiments, the age-related condition is selected from the group consisting of cancer, rheumatoid/osteoid arthritis, systemic lupus erythematosus (SLE), inflammatory bowel disease, Alzheimer's disease, multiple sclerosis, atherosclerosis, cardiovascular disease, cataracts, dementia, osteoporosis, type 2 diabetes, and hypertension. In some embodiments, the human subject is over the age of 35. In some embodiments, the human subject is over the age of 45. In some embodiments, the human subject is over the age of 55. In some embodiments, the human subject is over the age of 65.

Some embodiments disclosed herein provide methods for increasing the expression level of a gene in a human subject in need thereof, comprising: identifying a human subject having an increased expression level of APEX1; and delivering to the human subject an effective amount of a nitroxide antioxidant to increase the level of expression of the gene associated with apurinic/apyrimidinic endodeoxyribonuclease proteins and base excision repair activity. In some embodiments, the nitroxide antioxidant is 4-hydroxy-2,2,6, 6-tetramethylpiperidine-1-oxyl. In some embodiments, the increased expression level of the gene is age-related. In some embodiments, wherein the increased expression level of the gene is cancer-related. In some embodiments, the increased expression level of the gene is disease-related. In some embodiments, the increased expression level of the gene is neurodegeneration-related. In some embodiments, the increased expression level of the gene is infection related. In some embodiments, the increased the level of expression of the gene improves endodeoxyribonuclease activity and mitochondrial function. In some embodiments, the expression level of the gene is increased in a tissue selected from the group consisting of a skin tissue, an immune tissue, an adipose tissue, a pancreatic tissue, cardiac tissue, and a neuronal tissue by treatment.

Some embodiments disclosed herein provide methods for increasing an expression level, in an eukaryotic cell, of one or more genes encoding apurinic/apyrimidinic endodeoxyribonuclease proteins involved in base excision repair by contacting the eukaryotic cell with a nitroxide antioxidant. In some embodiments, the one or more genes is APEX1. In some embodiments, the nitroxide antioxidant is 4-hydroxy-2,2,6,6-tetramethylpiperidine-1-oxyl. In some embodiments, the eukaryotic cell is a cancer cell. In some embodiments, the expression level of the one or more genes is increased in said cell in a tissue selected from the group consisting of a skin tissue, an immune tissue, an adipose tissue, a pancreatic tissue, cardiac tissue, and a neuronal tissue. In some embodiments, prior to said contacting, the eukaryotic cell exhibits an age-related increased expression level of said one or more genes. In some embodiments, prior to said contacting, the eukaryotic cell exhibits a disease-related increased expression level of said one or more genes. In some embodiments, prior to said contacting, the eukaryotic cell exhibits a neurodegeneration-related expression level of said one or more genes.

Some embodiments disclosed herein provide methods for improving chemotherapeutic response in a human subject comprising: contacting cancer cells in the subject with an effective amount of a nitroxide antioxidant whereby a level of expression of apurinic/apyrimidinic endodeoxyribonuclease proteins and base excision repair activity is decreased in said cancer cells. In some embodiments, said cancer cells are known to have increased APEX1 function. In some embodiments, the decreased expression level of one or more genes following treatment initiates apoptosis within one or more of said cancer cells. In some embodiments, the decreased expression level reduces or prevents resistance to other chemotherapeutic agents. In some embodiments, the nitroxide antioxidant is 4-hydroxy-2,2,6,6-tetramethylpiperidine-1-oxyl. In some embodiments, the gene is selected from the group consisting of APEX1.

Some embodiments disclosed herein provide methods for increasing apurinic/apyrimidinic endodeoxyribonuclease proteins and base excision repair activity in a human subject comprising: identifying a human subject known to have increased APEX1 activity; and delivering to the subject an effective amount of a nitroxide antioxidant, whereby a level of apurinic/apyrimidinic endodeoxyribonuclease proteins and base excision repair activity is decreased. In some embodiments, the nitroxide antioxidant is 4-hydroxy-2,2,6, 6-tetramethylpiperidine-1-oxyl. In some embodiments, increased APEX1 function is age-related. In some embodiments, the increased APEX1 function is cancer-related. In some embodiments, the increased APEX1 function is disease-related. In some embodiments, the increased APEX1 function is neurodegeneration-related. In some embodiments, the increased APEX1 function is infection-related. In some embodiments, the increased level of expression of the gene improves remodeling of damaged tissues. In some embodiments, the expression level of the gene is increased in a tissue selected from the group consisting of a skin tissue, an immune tissue, an adipose tissue, a pancreatic tissue, cardiac tissue, and a neuronal tissue following treatment.

Some embodiments disclosed herein provide methods for treating a human subject having cancer comprising: delivering an effective amount of a nitroxide antioxidant to a human subject, wherein the human subject has previously been administered at least one chemotherapeutic agent, whereby a level of expression of apurinic/apyrimidinic endodeoxyribonuclease proteins and base excision repair activity is decreased. In some embodiments, the human subject having cancer is identified with a increased expression of APEX1. In some embodiments, the methods further comprise administering a promotor of a APEX1 to the human subject.

DETAILED DESCRIPTION

Definitions

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, N.Y. 1994); Sambrook et al., Molecular Cloning, A Laboratory Manual, Cold Springs Harbor Press (Cold Springs Harbor, N Y 1989). For purposes of the present disclosure, the following terms are defined below.

All patents, applications, published applications and other publications referred to herein are incorporated by reference for the referenced material and in their entireties. If a term or phrase is used herein in a way that is contrary to or otherwise inconsistent with a definition set forth in the patents, applications, published applications and other publications that are herein incorporated by reference, the use herein prevails over the definition that is incorporated herein by reference.

As used herein, the term "expression" means the detection of a gene product that is expressed or produced by a nucleic acid molecule by standard molecular biology methods, which gene product refers to e.g. an unspliced RNA, an mRNA, a splice variant mRNA, a polypeptide, a post-translationally modified polypeptide, a splice variant polypeptide etc., and specifically products made using an RNA gene product as a template, e.g. cDNA of the RNA.

As used herein, "differential expression" of a gene means that the expression of the gene is at a higher level ("decreased expression") or lower level ("decreased expression") in a human subject suffering from a disease, for example cancers and autoimmune diseases, relative to its expression in a normal or control subject. Differential expression includes both quantitative, as well as qualitative, differences in the temporal or cellular expression pattern in a gene or its expression products among, for example, normal and diseased cells, or among cells which have undergone different disease events or disease stages.

As used herein, "increasing the expression level" of a gene means causing the expression of the gene to decrease by treating the human subject with a compound, for example a nitroxide antioxidant, such that the expression level of the gene after treatment is lower than the expression level of the gene before treatment in the human subject.

As used herein, "delivering" a compound shall mean bringing that compound into contact with a relevant cell, tissue, or organism. Similarly, "contacting" shall mean that the compound contacts a relevant target, such as a tissue or cell or tumor. In either case, delivery or contact in an organism is affected by directly administering the compound to the organism, or by administering a different compound to the organism, such as a prodrug that is converted in vivo to the desired compound. In short, these terms cover any action that leads to contact between the desired compound and a target cell, tissue, or organism.

The present disclosure describes methods of modulating gene expression in human subjects. However, this is illustrative only and not intended to be limiting. For example, the methods disclosed herein can be used for modulating gene expression in other vertebrates, such as but not limited to mammals, birds, reptiles, fish, and the like (with modifications wherein appropriate). Mammals and birds include most agricultural animals. Treatment of companion animals, e.g., dogs, cats, or birds is also contemplated.

It is understood that aspects and embodiments of the invention described herein include "consisting" and/or "consisting essentially of" aspects and embodiments.

Other objects, advantages and features of the present invention will become apparent from the following specification taken in conjunction with the accompanying drawings.

Human Subject Identification

The present disclosure relates to methods of treating alteration in gene expression, such as age-related, cancer-related, disease-related, neurodegeneration-related, and infection-related alteration in gene expression. Gene expression changes also play important roles in aging and serve as biomarkers of physiological decline and disease conditions, such as neurodegenerative diseases, and cancers. Therefore, one aspect of the present disclosure is methods of treating a human subject having an age-related, cancer-related, disease-related, neurodegeneration related, and/or infection-related decrease in gene expression levels, such as those genes associated with apurinic/apyrimidinic endodeoxyribonuclease proteins and base excision repair activity. In some embodiments, the human subject can be identified based on the human subject's age, gene expression level, family history, health conditions, medical history, habits, or a combination thereof.

Regardless of the cause of the upregulation, some common terminology can be used. In some embodiments, the expression level of a gene (e.g., APEX1) in a human subject is considered to be upregulated or increased if the increase in the expression level of that gene is statistically significant compared to that of a control or a reference. In some embodiments, the expression level of a gene (e.g., APEX1) in a human subject is considered to be upregulated or increased if the increase in the expression level of that gene is statistically significant compared to that of a control or a reference.

In some embodiments, a normal healthy population or a population at large can be a population having the same or similar gender, age, and/or race, compared to the human subject. In some embodiments, the expression level of the gene in the control or reference can be the mean or median expression level of the gene in control subjects in the control or reference subjects in the reference. The increase in expression level can be statistically significant if the probability of the observed difference occurring not by chance, the confidence level, is greater than a threshold. The threshold can be, or be about, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.9%, or a number or a range between any two of these values.

In some embodiments, the increase in expression level can be, or be about, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 20%, 30%, 40%, 50%, 60%, 70%, 80%, 90%, 100%, or a number or a range between any two of these values. In some embodiments, the increase in expression level can be at least 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 20%, 30%, 40%, 50%, 60%, 70%, 80%, 90%, 100%, or more.

In some embodiments, the human subject may have an age that is, is about, or is over 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 years old.

In some embodiments, the human subject is identified based on the human subject's expression profiles of APEX1. Non-limiting exemplary methods for determining the human subject's expression profiles include: amplification techniques such as PCR and RT-PCR (including quantitative variants), hybridization techniques such as in situ hybridization, microarrays, blots, and others, and high throughput sequencing techniques like Next Generation Sequencing (Illumina, Roche Sequencer, Life Technologies SOLID™), Single Molecule Real Time Sequencing (Pacific Biosciences), True Single Molecule Sequencing (Helicos), or sequencing methods using no light emitting technologies but other physical methods to detect the sequencing reaction or the sequencing product, like Ion Torrent (Life Technologies). Non-limiting exemplary methods for determining the human subject's expression profiles include: binding techniques such as ELISA, immunohistochemistry, microarray and functional techniques such as enzymatic assays.

Targeted Gene Expression Adjustment

The development and progression of all disease results from a dysfunction of one or more genes involved in the biological processes associated with a disease or condition. Traditionally, a diagnosable disease or condition required a patient to present with a symptom of the disease. This approach fails to consider the underlying cause of cellular dysfunction that resulted in the symptom. In this way, current therapeutic strategies are generally ineffective regarding the treatment of a cause of the disease because they fail to target and correct the dysfunction of the genes that cause the disease. Instead, a disease is best defined by the identifying the dysfunctional gene that causes the disease and correcting the expression level of that gene to a healthy state.

The human genome is comprised of over 20,000 genes and each of them provide instructions necessary for the formation and function of proteins. Genes are the foundation of all cellular composition and function. They contain provide all necessary instruction for the healthy function and formation of proteins. Every component of a cell exists and operates based on the instruction provided by genes, and each cell communicates and interacts with each other to form tissues and control the healthy function of the human body. Even extracellular molecules are created and released based on the expression levels of genes controlling the formation and release from the cell. Certain biological processes rely on extracellular molecules to engage cell-surface receptors that transmit a signal into the cell and every step of this process is controlled by the genes associated with that biological process. While biological processes may be complicated, gene expression provides a fundamental ability to focus on the precise cause of a switch from healthy biological activity to a disease state.

Every disease and condition can be traced back to a dysfunction in one or more genes that prevents their ability to maintain a healthy state for an individual. One of the most common dysfunctions related to the expression level of a gene. Genes are expressed in a regulated manner to control the amount of instruction they provide. The quantity of gene expression correlates with the quantity of proteins formed within a cell, as well as modulates the activity of each protein.

Overexpression of a gene causes diseases by overproducing proteins and increasing the activity of the proteins which leads to signs and symptoms identifiable as a disease. Conversely, when a gene is underexpressed, the encoded proteins are reduced and their functions are inhibited resulting in diminished function of the cell and identifiable characteristics of a disease.

In a healthy state, genes are expressed in a regulated manner that maintains or promotes healthy function of the cell. When a gene is inappropriately expressed, the cell may try to compensate by upregulating or downregulating other genes. However, the cell cannot maintain compensatory mechanisms indefinitely and the cell will eventually succumb to the disease state caused by the inappropriate gene expression, that can result in nearby cells being affected in a similar way. In order to treat or prevent a disease or condition, the underlying dysfunction of the genes must be identified and corrected by modulating the gene expression to a healthy state.

Diseases and conditions exploit gene dysfunctional expression to advance the disease by regulating cellular function to promote the needs of the disease state occurring within the cell. Cancer provides an example of modified cellular activity to promote the development of tumors, increased cellular metabolism, and resistance to therapies or mutational burdens due to the rapid uncontrolled growth of cancer cells. In particular, cancer cells increase activity relating to base excision repair by upregulating genes that provide instructions for proteins to identify and remove lesions in the DNA. By upregulating base excision repair, cancer cells protect themselves against apoptosis otherwise caused by the damages in the cancer cell DNA.

In a healthy state, a predictable amount of interaction and activation of downstream factors are regulated by APEX1 expression. When these proteins are overexpressed, their corresponding function becomes hyperactive causing diseases associated with APEX1. While the disease or condition may be diagnosed based on clinical presentation of symptoms, the cause of the disease is the overexpression of the APEX1 gene that resulted in the hyperactivity of the protein. Therefore, the disease is better diagnosed as an overexpression of the APEX1 gene. Once the dysfunctional gene has been identified administering a treatment focused on modulating the gene expression towards a healthy level treats, or prevents, the disease.

Certain conditions, such as cardiovascular diseases, diabetes, obesity, and aging are associated with (e.g., causes or caused by) underexpression of apurinic/apyrimidinic endodeoxyribonuclease protein encoding genes resulting in the inhibition, inactivity, and disfunction of vital cellular processes within cells and tissues. Thus, modulation of underexpressed apurinic/apyrimidinic endodeoxyribonuclease protein genes is essential for treatment and prevention of certain conditions.

Genes Associated with Apurinic/Apyrimidinic Endodeoxyribonuclease Proteins and Base Excision Repair Activity In some embodiments, administering to the human subject an effective amount of the nitroxide antioxidant results in a decreased expression level of a gene, for example APEX1. Therefore, some embodiments disclosed herein provide methods for treating an individual in need thereof, comprising identifying an individual having a disease-related increased expression level of APEX1; and administering to the individual an effective amount of a nitroxide antioxidant to decrease the level of expression of APEX1. Some embodiments disclosed herein provide methods for treating an individual in need thereof, comprising identifying an individual in need of a decreased expression level of a APEX1 gene; and administering to the individual an effective amount of a nitroxide antioxidant to decrease the level of expression of APEX1. Some embodiments disclosed herein provide methods for treating an individual in need thereof, comprising: administering to the individual, known to have a disease-related increased expression level of APEX1, an effective amount of a nitroxide antioxidant to increase the level of expression of APEX1. Some embodiments disclosed herein provide methods for treating an individual in need thereof, comprising: administering to an individual, known to be in need of a decreased expression level of a APEX1 gene, an effective amount of a nitroxide antioxidant to increase the level of expression of apurinic/apyrimidinic endodeoxyribonuclease proteins and base excision repair activity.

Non-limiting examples of diseases associated with altered level of apurinic/apyrimidinic endodeoxyribonuclease proteins and base excision repair activity include cancer; breast cancer; lung cancer; kidney cancer; cancers of the ovary and uterus; cancer of the central nervous system; cancers of the head and neck; melanoma; lymphomas; leukemia; neurological disorders; Alzheimer's disease; Parkinson's disease; Huntington's disease; amyotrophic lateral sclerosis; stroke;

cardiovascular disorders; ischemia; heart failure; infections, infectious diseases; bacterial infections; inflammatory responses; viral infections; autoimmune diseases; systemic lupus erythematosus; autoimmune lymphoproliferative syndrome; rheumatoid arthritis; and thyroiditis.

The genes associated with base excision repair encode proteins that can be DNA glycosylases, AP endonucleases, DNA polymerases, Flap endonucleases, DNA ligases, MBD4, NEIL1. For example, the treatment results in decreased expression levels of APEX1. The a decreased expression level of APEX1, decreases apurinic/apyrimidinic endodeoxyribonuclease proteins and apurinic/apyrimidinic endodeoxyribonuclease protein. The decreased level of APEX1 results in a decrease in or disappearance of signs and symptoms of a disease associated with increased APEX1 function, including the curing of the disease associated with increased APEX1 function. In some embodiments, the decreased expression level of APEX1, decreases the level of apurinic/apyrimidinic endodeoxyribonuclease proteins and base excision repair activity. The decreased level of apurinic/apyrimidinic endodeoxyribonuclease proteins and base excision repair activity results in a decrease in or disappearance of signs and symptoms of the disease associated with increased APEX1 function, including the curing of the disease associated with increased APEX1 function. In some embodiments, the decreased level of apurinic/apyrimidinic endodeoxyribonuclease proteins and base excision repair activity inhibits, suppress, prevents, or reverses the disease or the symptoms associated with the disease.

Base Excision Repair

Base excision repair (BER) is a highly conserved mechanism dealing with oxidative damage generated by respiration, natural hydrolysis and alkylation reactions that occur in each cell, many thousands of times a day. In humans at least 30 proteins are involved in both short patch repair, the removal of a single non-bulky damaged base; and long patch repair, where 2-8 nucleotides are synthesised to displace the damaged area. The first step of the BER pathway is the recognition and removal of base damage by damage-specific DNA glycosylases. Humans have 11 DNA glycosylases that can be subdivided into three groups: 1 Monofunctional enzymes which excise the damaged base leaving an apurinic/apyrimidinic (AP) site and an intact phosphodiester backbone; 2 Bifunctional glycosylases that remove the base and cleave the phosphodiester bond on the 3' side of the damaged base creating an 3'-α,β-unsaturated aldehyde (β-elimination); and 3 Nei-like DNA glycolysases (NEIL) that can catalyse a β/δ-elimination reaction where the phosphodiester bond is cleaved either side of the removed lesion. (Gabrielle J. Grundy, Jason L. Parsons; Base excision repair and its implications to cancer therapy. Essays Biochem 26 Oct. 2020; 64 (5): 831-843. doi: https://doi.org/10.1042/EBC20200013).

The following are additional examples of additional proteins involved in the BER pathway are UNGs or UDGs, are uracil-DNA glycosylases and are evolutionary, well-preserved DNA-repair enzymes. The term UDG refers to a superfamily of enzymes comprising six sub-families. Family I UDG enzymes are called UNG, after the uracil-N-glycosylase gene. SMUG1, Single-strand selective monofunctional uracil DNA glycosylase which removes uracil through base excision repair. SMUG1 also processes radiation-induced oxidative base damage as well as 5-fluorouracil incorporated into DNA during chemotherapy. TDG, G/T Mismatch specific thymine DNA glycosylase plays a central role in the pathways for 5-methyl cytosine removal and thus influences gene silencing, stem cell differentiation, and alterations in normal development. Additionally, methylation abnormalities in DNA are often observed in diseases, specifically cancer. MBD4, Methyl-CpG binding domain protein 4 is a mismatch-specific DNA N-glycosylase involved in DNA repair. It has thymine glycosylase activity and is specific for G:T mismatches within methylated and unmethylated CpG sites. Other BER proteins include MPG, N-methylpurine DNA glycosylase, MUTYH, Adenine DNA glycosylase, NTH1, Endonuclease III-like protein 1, OGG18, oxoguanine DNA glycosylase 1, NEIL1, NEIL2, and NEIL3.

Apurinic/Apyrimidinic Deoxyriboendonuclease 1

Apurinic/Apyrimidinic Deoxyriboendonuclease 1 is encoded by the APEX1/APE1/REF-1 gene in human cells. APEX1 is also known as APE1, HAP1, APEN. This endonuclease is an enzyme involved in targeting and removing DNA lesions, particularly at apurinic/apyrimidinic (AP) locations of the DNA. Such AP activity sites occur frequently in DNA molecules by spontaneous hydrolysis, by DNA damaging agents or by DNA glycosylases that remove specific abnormal bases.

APE1 acts as a master regulator of cellular transcription, by modulating in a redox-dependent and independent fashion the DNA binding activity of several cancer-related transcription factors including NF-κB, Egr-1, p53, HIF-1α, and others. (Poletto, Mattia et al. "Inhibitors of the apurinic/apyrimidinic endonuclease 1 (APE1)/nucleophosmin (NPM1) interaction that display anti-tumor properties." Molecular carcinogenesis vol. 55,5 (2016): 688-704. doi: 10.1002/mc.22313).

In a healthy state, APEX1 is a component of the base excision repair pathway and promotes removal of damaged areas of DNA to promote healthy cellular function. When APEX1 expression is elevated or over expressed, the base excision repair process can increase to promote dysfunctional cells by preventing apoptosis and advancing the progression of a disease and condition.

Cancer cells often rely on increased BER activity to tolerate oxidative stress. Targeting BER has been an attractive strategy to overwhelm cancer cells with DNA damage, improve the efficacy of radiotherapy and/or chemotherapy, or form part of a lethal combination with a cancer specific mutation/loss of function. By increasing or upregulating BER activity through overexpression of one or more BER associated proteins, diseases regulate ability to prevent apoptosis and advance the disease progression through increased management of mutations in the DNA.

APEX1 expression has been shown to be upregulated or overexpressed in several diseases and conditions, where the increased expression of the gene causes overactivity of the encoded protein. Whether the overexpression is endogenous or exogenous, overactive APEX1 is directly links to the cause and progression of cancer, diabetes, neurodegenerative disorders, heart disease, and eye disease.

APEX1 Activation of NRF2

APEX1 also known as Redox factor-1 (Ref-1) has several functions in addition to DNA repair function controls the activity of multiple transcription factors, including NF-κB (nuclear factor-KB), STAT3, AP-1 (activator protein-1), and HIF-1 (hypoxia inducible factor). In particular, it is the redox activity of Ref-1 that reduces specific cysteine residues in the DNA binding domain of these transcription factors, thereby stimulating their DNA binding activity. As most transcription factors stimulated by Ref-1 are well recognized regulators of tumorigenesis, this protein has emerged as a viable therapeutic target in cancer. (Fishel, Melissa L et al. "Apurinic/apyrimidinic endonuclease/redox factor-1 (APE1/Ref-1) redox function negatively regulates NRF2." The Journal of biological chemistry vol. 290,5 (2015): 3057-68. doi:10.1074/jbc.M114.621995). APEX1/REF1 activates NRF2 in an oxidative stress independent manner. Generally, NRF2 is activated in the presence of oxidative stress such that NRF2 regulates ROS to reduce and modulate the impact ROS have. The inverse relationship between REF1 and NRF2 show that by administering a nitroxide antioxidant to a patient with oxidative stress, NRF2 is activated in a novel manner to prevent and reduce the oxidative stress by promoting NRF2 activity.

Cancer

There are several properties common across most types of cancer. They display unrestrained cell proliferation, perpetual replication, sustained angiogenesis, the ability to escape apoptosis and invasiveness. One method to fight cancer is to exploit differences between normal cells and the cancer cells so they can be selectively destroyed. Many cancers are able to avoid or escape apoptosis due to abnormal DNA damage responses. Radiation and chemotherapy are generally directed towards inducing massive amounts of oxidative stress causing breaks and damage to the DNA causing cancer cell death. However, cancers are often resistant or develop resistance to these treatments due to the cancer cells' remarkable ability to adapt their DNA damage responses to compensate for any shortcomings.

Regarding base excision repair in cancer, the BER pathway repairs alkylated, oxidative and IR-induced damage. There are two branches of the BER pathway, long-patch and short-patch BER, which will be discussed here. Alkylated or oxidative damage can cause single-base lesions or adducts. The BER pathway is initiated when DNA glycosylases specific to each type of lesion recognize and remove the damaged base. This generates an abasic or apurinic/apyrimidinic (AP) site. (Reed, April M et al. "Small-molecule inhibitors of proteins involved in base excision repair potentiate the anti-tumorigenic effect of existing chemotherapeutics and irradiation." Future oncology (London, England) vol. 5,5 (2009): 713-26. doi:10.2217/fon.09.31).

PARP-inhibitors are an example of the importance for targeting specific pathways involved in BER. PARP is an important protein in DNA repair pathways especially the BER. BER is involved in DNA repair of single strand breaks (SSBs). If BER is impaired, inhibiting poly(ADP-ribose) polymerase (PARP), SSBs accumulate and become double stand breaks (DSBs). The cells with increasing number of DSBs become more dependent on other repair pathways, mainly the homologous recombination (HR) and the non-homologous end joining. APEX1 used separately or in combination with a PARP inhibitor provides additional benefit in anti-cancer and anti-tumor activity by inhibiting compensatory mechanisms by the cancer cells to adjust for the diminished BER activity.

Decreasing or inhibiting APEX1 is known to have anti-tumor activity. In particular, inhibiting APEX1 disrupts the metabolic pathway for tumor cells in colorectal cancer. Colorectal cancer (CRC) is considered the third most common cancer and the fourth most common cause of cancer-related death worldwide. About 70% of CRC patients suffer from a sporadic form, whereas 10-30% present a familial predisposition and only 5-7% exhibit an inherited trait. common mutations in all CRC patients may include dysfunction in genes encoding proteins such as APC, PTEN, SMAD4, TGFBR2, TP53, BRAF, KRAS, and PIK3CA. Recent studies have shown the involvement of DNA repair genes has been demonstrated to be associated with the pathogenesis of CRC. In particular, both endogenous (e.g. metabolic activity of the cells) and exogenous factors (e.g. food intake) are involved in DNA damage, which requires the activation of the DNA repair mechanisms. In particular, the base excision repair (BER) pathway is involved in repairing DNA chemical modifications, such as deamination, oxidation, and alkylation. (Codrich, Marta et al. "Inhibition of APE1-endonuclease activity affects cell metabolism in colon cancer cells via a p53-dependent pathway." DNA repair vol. 82 (2019): 102675. doi:10.1016/j.dnarep.2019.102675).

APE1 is implicated in cancer gene expression regulation due to its role as a redox co-activator of several transcription factors, such as Egr-1, NF-κB, p53, STAT3, HIF-1α, CREB, AP-1, and Pax-5/8. APE1 is considered as a unique nuclear redox-signaling factor bearing seven cystine residues. (Codrich, 2019). Interaction between APE1 and Nucleophosmin (NPM1) is essential for the subcellular localization of APE1 modulating its endonuclease activity. (Id). NPM1 gene is up-regulated, mutated and chromosomally translocated in many tumor types. Chromosomal aberrations involving NPM1 were found in patients with non-Hodgkin lymphoma, acute promyelocytic leukemia, myelodysplastic syndrome, and acute myelogenous leukemia. [7] Heterozygous mice for NPM1 are vulnerable to tumor development. In solid tumors NPM1 is frequently found overexpressed, and it is thought that NPM1 could promote tumor growth by inactivation of the tumor suppressor p53/ARF pathway; on the contrary, when expressed at low levels, NPM1 could suppress tumor growth by the inhibition of centrosome duplication. NPM1 stimulates APE1 endonuclease activity on abasic double-stranded DNA. Where NPM1 interacts with APE1, carcinogenesis and tumorigenesis is promoted. The upregulation of APE1 by NPM1 is counteracted by administration of a nitroxide antioxidant administered in therapeutically effective amounts sufficient to decrease expression of APE1.

Of high importance is NPM involvement in acute myelogenous leukemia, where a mutated protein lacking a folded C-terminal domain (NPM1c+) has been found in the cytoplasm in patients. This aberrant localization has been linked to the development of the disease, and is associated with improved clinical outcomes. Strategies against this subtype of acute myelogenous leukemia include the refolding of the C-terminal domain using pharmacological chaperones and the displacement of the protein from nucleolus to nucleoplasm, which has been linked to apoptotic mechanisms. It has also been shown that in the context of clonal hematopoiesis of undetermined significance harboring a DNMT3A mutation, subsequent NPM1 mutations drive progression into overt myeloproliferative neoplasm.

Inhibition and decrease in APE1 expression decreases the associated activities of APEL. In cancer, these decreased activities prevent tumor growth, cancer formation, and promote apoptosis after metabolic disruption.

There are several mechanisms whereby increased or overexpression of APEX1 promotes caner development and progression. As described, inhibition of APEX1 prevents disease progression by promoting apoptosis of cancer cells, reduces metabolic activity, promotes or re-establishes chemosensitivity, and prevents management of ROS in cancer cells.

Eye Disease

Ocular neovascular diseases like wet age-related macular degeneration are a major cause of blindness. Ocular neo-vascularization is the key pathobiological feature of diseases like proliferative diabetic retinopathy (PDR), retinopathy of prematurity (ROP), and wet age-related macular degeneration (AMD), which together are major causes of blindness (Campochiaro, 2013). In PDR and ROP, abnormal blood vessels grow in and on the retina, and in wet AMD, neovessels grow from the pigmented, subretinal choroid layer into the retina. In all cases, neovessels disrupt retinal architecture and can hemorrhage, leading to blindness. Although the exact stimuli promoting neovascularization are not always well characterized, hypoxia and inflammation both play crucial roles. The currently used, Food and Drug Administration-approved pharmacological treatments for these diseases are all biologics targeting the vascular endothelial growth factor (VEGF) signaling pathway, such as ranibizumab and aflibercept (Prasad et al., 2010). Although these therapeutic agents have been very successful, significant proportions of patients are resistant and refractory (Lux et al., 2007; Falavarjani and Nguyen, 2013). Moreover, serious side effects including hemorrhage and endophthalmitis are possible. Therefore, development of novel therapeutic approaches targeting other signaling pathways is crucial. (Ref-1/APE1 Inhibition with Novel Small Molecules Blocks Ocular Neovascularization, Sheik Pran Babu Sardar Pasha, Kamakshi Sishtla, Rania S. Sulaiman, Bomina Park, Trupti Shetty, Fenil Shah, Melissa L. Fishel, James H. Wikel, Mark R. Kelley and Timothy W. Corson. Journal of Pharmacology and Experimental Therapeutics October 2018, 367 (1) 108-118; DOI: https://doi.org/10.1124/jpet.118.248088).

APEX1/REF1 is a redox-sensitive transcriptional activator for nuclear factor (NF)-κB and other proangiogenic transcription factors. antiangiogenic effects by blocking the activation of transcription factors induced by Ref-1. This includes NF-κB as shown, and HIF-1α; both of these can regulate VEGF (Forsythe et al., 1996). Ref-1/APE1 is highly expressed during retinal development, and in retinal pigment epithelium cells, pericytes, choroidal endothelial cells, and retinal endothelial cells (Chiarini et al., 2000). More generally, Ref-1 is frequently upregulated in regions of tissues in which inflammation is present (Zou et al., 2009).

By decreasing expression levels of APEX1, regulation of downstream transcriptions factors confers a benefit to individuals having eye disease. More importantly, the decrease of APEX1 expression directly correlates with increased NRF2 and decreased NFkB prior to development of a disease, thereby preventing the development and progression of such disease.

Methods for Treating Genetic Diseases Associated with Increased APEX1 Activity

Some embodiments disclosed herein provide methods for treating genetic diseases associated with increased APEX1 activity in a human subject in need thereof, comprising (optionally) identifying a human subject having a genetic disease and in need of a decreased expression level of a APEX1 gene; and administering to the human subject an effective amount of a nitroxide antioxidant. In some embodiments, the methods disclosed herein are used to treat a human subject that shows no symptoms of the genetic disease, but is at risk of having the genetic disease. Exemplary risk factors for genetic diseases include, but are not limited to, age, family history, health conditions, medical history, habits, or a combination thereof. In some embodiments, risk factors for genetic disease comprise an increased expression level of APEX1.

In some embodiments, administering to the human subject an effective amount of the nitroxide antioxidant results in a decreased expression level of a gene, for example APEX1. The gene associated with apurinic/apyrimidinic endodeoxyribonuclease protein 2 can be APEX1, APE1, HAP1, APEN, DNA glycosylases, AP endonucleases, DNA polymerases, Flap endonucleases, DNA ligases, MBD4, NEILL. The treatment of the human subject with the effective amount of the nitroxide antioxidant results in a decreased expression level of the gene. For example, the treatment results in a decreased expression level of APEX1. The decreased expression level of APEX1, decreases the quantity of the encoded protein and improves base excision repair activity activated by increased expression levels. The improved and corrected endodeoxyribonuclease activity and base excision repair function reduces, prevents, or eliminates the signs and symptoms of a genetic disease associated with increased APEX1 function, including the curing of the genetic disease.

In some embodiments, the levels of APEX1 in the connective tissue, muscle tissue, nervous tissue, and/or epithelial tissue change after the nitroxide antioxidant is administered. Non-limiting examples of the connective tissue include dense connective tissue, loose connective tissue, reticular connective tissue, adipose tissue, cartilage, bone, and extracellular matrix. Non-limiting examples of the muscle tissue includes smooth muscle tissue, cardiac muscle tissue, and skeletal muscle tissue. Non-limiting examples of the nervous tissue include neural tissue of the central nervous system, neural tissue of the peripheral nervous system, the brain, spinal cord, cranial nerves, spinal nerves, and motor neurons. Non-limiting examples of the epithelial tissue include squamous epithelium, cuboidal epithelium, columnar epithelium, glandular epithelium, ciliated epithelium, and skin.

Non-limiting examples of genetic diseases associated with increased APEX1 activity include Osteogenesis imperfecta, Spondyloepiphyseal dysplasia, Spondyloepimetaphyseal dysplasia, Achondrogenesis, hypochondrogenesis, Kniest dysplasia, Stickler syndrome, Ehlers-Danlos syndrome, Familial porencephaly, Hereditary angiopathy with nephropathy, aneurysms and muscle cramps syndrome, Benign familial haematuria, Alport syndrome, Leiomyomatosis, Bethlem myopathy, Ullrich congenital muscular dystrophy, Dystrophic epidermolysis bullosa, Corneal endothelial dystrophies Multiple epiphyseal dysplasia, Autosomal recessive Stickler syndrome, Schmid metaphyseal chondrodysplasia, Marshall syndrome, Otospondylomegaepiphyseal dysplasia Deafness, Junctional epidermolysis bullosa-other Knobloch syndrome Methods for Counteracting Treating a Disease Related to Aging Some embodiments disclosed herein provide methods for counteracting age-related increase in gene expression or treating an age-related disease, comprising (optionally) identifying a human subject over the age of 35 and having an increased expression level of APEX1 or an age-related disease; and administering to the human subject an effective amount of a nitroxide antioxidant. In some embodiments, the methods comprise determining the expression level of APEX1. The identification step and/or the determination step may not be necessary in some instances, such as where an increased expression level of APEX1 can be inferred from the human subject's age, family history, health conditions, medical history, habits, or a combination thereof. In some embodiments, the methods disclosed herein are used to treat a human subject shows no symptoms of an age-related disease, but is at risk of having an age-related disease. Exemplary risk factors for an age-related disease include, but are not limited to, age, family history, health conditions, medical history, habits, or a combination thereof.

In some embodiments, risk factors for an age-related disease comprise a increased expression level of APEX1.

In some embodiments, administering to the human subject an effective amount of the nitroxide antioxidant results in a decreased expression level of a gene, for example APEX1. The genes associated with base excision repair encode proteins that can be DNA glycosylases, AP endonucleases, DNA polymerases, Flap endonucleases, DNA ligases, MBD4, NEIL1, or a homologue thereof. The treatment of the human subject with the effective amount of the nitroxide antioxidant results in a decreased expression level of the gene. For example, the treatment results in a decreased expression level of APEX1. The decreased expression level of APEX1, corrects base excision repair function and endodeoxyribonuclease activity to a healthy level within the cell. The corrected level of endodeoxyribonuclease activity and base excision repair function results in a decrease in or disappearance of signs and symptoms of an age-related disease associated with increased APEX1 function, including the curing of the age-related disease.

In some embodiments, the levels of APEX1 in the connective tissue, muscle tissue, nervous tissue, and/or epithelial tissue change after the nitroxide antioxidant is administered. Non-limiting examples of the connective tissue include dense connective tissue, loose connective tissue, reticular connective tissue, adipose tissue, cartilage, bone, and extracellular matrix. Non-limiting examples of the muscle tissue includes smooth muscle tissue, cardiac muscle tissue, and skeletal muscle tissue. Non-limiting examples of the nervous tissue include neural tissue of the central nervous system, neural tissue of the peripheral nervous system, the brain, spinal cord, cranial nerves, spinal nerves, and motor neurons. Non-limiting examples of the epithelial tissue include squamous epithelium, cuboidal epithelium, columnar epithelium, glandular epithelium, ciliated epithelium, and skin.

Some embodiments disclosed herein provide methods for treating a disease related to aging in a human subject in need thereof, comprising (optionally) identifying a human subject over the age of 35 and having an age-related disease and having an increased expression level of the APEX1 gene; and administering to the human subject an effective amount of a nitroxide antioxidant. Some embodiments disclosed herein provide methods for treating an individual having or at risk of developing a condition due to aging, comprising: identifying an individual over the age of 35; and administering to the individual an effective amount of a nitroxide antioxidant, whereby the expression level of the gene associated with apurinic/apyrimidinic endodeoxyribonuclease protein 2 is decreased.

Non-limiting examples of age-related diseases include cancer, rheumatoid/osteoid arthritis, systemic lupus erythematosus (SLE), inflammatory bowel disease, Alzheimer's disease, multiple sclerosis, atherosclerosis, cardiovascular disease, cataracts, dementia, osteoporosis, type 2 diabetes, hypertension.

Methods for Increasing Expression Level of a Gene

Some embodiments disclosed herein provide methods for increasing the expression level of a gene in a human subject in need thereof, comprising (optionally) identifying a human subject having an increased expression level of a APEX1 gene; and administering to the human subject an effective amount of a nitroxide antioxidant. Some embodiments disclosed herein provide methods for treating a disease associated with increased APEX1 activity in a patient in need thereof, comprising (optionally) identifying a human subject having an increased expression level of APEX1; and administering to the human subject an effective amount of a nitroxide antioxidant. The increased expression level may be age-related, or disease related. In some embodiments, the disease is cancer, rheumatoid/osteoid arthritis, systemic lupus erythematosus (SLE), inflammatory bowel disease, Alzheimer's disease, multiple sclerosis, atherosclerosis, cardiovascular disease, cataracts, dementia, osteoporosis, type 2 diabetes, hypertension, or any combination thereof. Some embodiments disclosed herein provide methods for treating an individual in need thereof, comprising (optionally) identifying a human subject over the age of 35 in need of a decreased expression level of a APEX1 gene; and administering to the human subject an effective amount of a nitroxide antioxidant. In some embodiments, the methods comprise determining the expression level of APEX1. In some embodiments, the determination step comprises inferring increased expression level of APEX1 based on the human subject's age, family history, health conditions, medical history, habits, or a combination thereof. In some embodiments, the methods disclosed herein may be used to treat a human subject shows no symptoms of a disease associated with increased APEX1 function, but is at risk of having a disease associated with increased APEX1 function. Exemplary risk factors for a disease associated with increased APEX1 function include, but are not limited to, age, family history, health conditions, medical history, habits, or a combination thereof.

In some embodiments, administering to the human subject an effective amount of the nitroxide antioxidant results in a decreased expression level of a gene, for example a gene associated with base excision repair activity. The gene associated with apurinic/apyrimidinic endodeoxyribonuclease protein 2 can be APEX1. The treatment of the human subject with the effective amount of the nitroxide antioxidant results in a decreased expression level of the gene. For example, the treatment decreases the expression levels of APEX1. The decreased expression of the gene counteracts the increase in the expression level of the gene.

Methods for Treating Cancer

Some embodiments disclosed herein provide methods for treating cancer in a human subject in need thereof, comprising (optionally) identifying a human subject having a cancer and in need of a decreased expression level of a APEX1 gene; and administering to the human subject an effective amount of a nitroxide antioxidant. In some embodiments, the methods disclosed herein may be used to treat a human subject that shows no symptoms of cancer, but is at risk of having cancer. Exemplary risk factors for cancer include, but are not limited to, age, family history, health conditions, medical history, habits, or a combination thereof. In some embodiments, risk factors for cancer comprise a decreased expression level of APEX1.

Non-limiting examples of the methods for identifying a human subject having a cancer include colonoscopy; sigmoidoscopy; and high-sensitivity fecal occult blood tests. In some embodiments, methods for identifying a human subject having a cancer include low-dose helical computed tomography; mammography; and pap test and human papillomavirus (HPV) testing. In some embodiments, methods for identifying a human subject having a cancer include alpha-fetoprotein blood test; breast magnetic resonance imaging (MRI); CA-125 test; clinical breast exams and regular breast self-exams; prostate-specific antigen (PSA) testing; skin exams; transvaginal ultrasound; and virtual colonoscopy. In some embodiments, methods for identifying a human subject having a cancer include barium enema; biopsy; bone marrow aspiration and biopsy; bone scan;

breast MRI for early detection of breast cancer; breast MRI; colonoscopy; computed tomography (CT) scan; digital rectal exam (DRE); blood and platelets testing; bone marrow testing; umbilical cord blood testing; electrocardiogram (EKG) and echocardiogram; endoscopic techniques; fecal occult blood tests; magnetic resonance imaging (MRI); mammography; multi gated acquisition (MUGA) scan; papanicolaou (pap) test; positron emission tomography and computed tomography (PET-CT) scan; sigmoidoscopy; tumor marker tests; ultrasound; upper endoscopy. In some embodiments, methods for identifying a human subject having a cancer include DNA sequencing; detecting presence of single nucleotide polymorphism (SNIP); and detecting the presence of certain protein markers.

In some embodiments, administering to the human subject an effective amount of the nitroxide antioxidant results in a decreased expression level of a gene, for example a gene associated with base excision repair activity. The genes associated with base excision repair encode proteins that can be DNA glycosylases, AP endonucleases, DNA polymerases, Flap endonucleases, DNA ligases, MBD4, NEIL1, or a homologue thereof. The treatment of the human subject with the effective amount of the nitroxide antioxidant results in a decreased expression of the gene. For example, the treatment results in a decreased expression level of APEX1. The decreased expression level of the gene can modulate base excision repair function and endodeoxyribonuclease activity to a healthy rate and function. The improved base excision repair function and endodeoxyribonuclease activity results in a decrease in or disappearance of signs and symptoms of the cancer, including the curing of the cancer.

Non-limiting examples of cancer include bladder and other urothelial cancers; breast cancer; cervical cancer; colorectal cancer; endometrial cancer; endometrial cancer; esophageal cancer; liver (hepatocellular) cancer; lung cancer; neuroblastoma cancer; oral cavity and oropharyngeal cancer; ovarian, fallopian tube, and primary peritoneal cancer; prostate cancer; skin cancer; stomach (gastric) cancer; and testicular cancer.

Non-limiting examples of cancer include acute lymphoblastic leukemia, adult; acute myeloid leukemia, adult; adrenocortical carcinoma; aids-related lymphoma; anal cancer; bile duct cancer; bladder cancer; brain tumors, adult; breast cancer; breast cancer and pregnancy; breast cancer, male; carcinoid tumors, gastrointestinal; carcinoma of unknown primary; cervical cancer; chronic lymphocytic leukemia; chronic myelogenous leukemia; chronic myeloproliferative neoplasms; cns lymphoma, primary; colon cancer; endometrial cancer; esophageal cancer; extragonadal germ cell tumors; fallopian tube cancer; gallbladder cancer; gastric cancer; gastrointestinal carcinoid tumors; gastrointestinal stromal tumors; germ cell tumors, extragonadal; germ cell tumors, ovarian; gestational trophoblastic disease; hairy cell leukemia; hepatocellular (liver) cancer, adult primary; histiocytosis, langerhans cell; hodgkin lymphoma, adult; hypopharyngeal cancer; intraocular (eye) melanoma; islet cell tumors, pancreatic neuroendocrine tumors; kaposi sarcoma; kidney (renal cell) cancer; kidney (renal pelvis and ureter, transitional cell) cancer; langerhans cell histiocytosis; laryngeal cancer; leukemia, adult acute lymphoblastic; leukemia, adult acute myeloid; leukemia, chronic lymphocytic; leukemia, chronic myelogenous; leukemia, hairy cell; lip and oral cavity cancer; liver cancer, adult primary; lung cancer, non-small cell; lung cancer, small cell; lymphoma, adult Hodgkin; lymphoma, adult non-hodgkin; lymphoma, aids-related; lymphoma, primary cns; malignant mesothelioma; melanoma; melanoma, intraocular (eye); merkel cell carcinoma; metastatic squamous neck cancer with occult primary; multiple myeloma and other plasma cell neoplasms; mycosis fungoides and the sézary syndrome; myelodysplastic syndromes; myelodysplastic/myeloproliferative neoplasms; myeloproliferative neoplasms, chronic; paranasal sinus and nasal cavity cancer; nasopharyngeal cancer; neck cancer with occult primary, metastatic squamous; non-hodgkin lymphoma, adult; non-small cell lung cancer; oral cavity cancer, lip oropharyngeal cancer; ovarian epithelial cancer; ovarian germ cell tumors; ovarian low malignant potential tumors; pancreatic cancer; pancreatic neuroendocrine tumors (islet cell tumors); pheochromocytoma and paraganglioma; paranasal sinus and nasal cavity cancer; parathyroid cancer; penile cancer; pheochromocytoma and paraganglioma; pituitary tumors; plasma cell neoplasms, multiple myeloma and other; breast cancer and pregnancy; primary peritoneal cancer; prostate cancer; rectal cancer; renal cell cancer; transitional cell renal pelvis and ureter; salivary gland cancer; sarcoma, Kaposi; sarcoma, soft tissue, adult; sarcoma, uterine; mycosis fungoides and the sézary syndrome; skin cancer, melanoma; skin cancer, nonmelanoma; small cell lung cancer; small intestine cancer; stomach (gastric) cancer; testicular cancer; thymoma and thymic carcinoma; thyroid cancer; transitional cell cancer of the renal pelvis and ureter; trophoblastic disease, gestational; carcinoma of unknown primary; urethral cancer; uterine cancer, endometrial; uterine sarcoma; vaginal cancer; and vulvar cancer.

In some embodiments, non-limiting examples of cancer include, but are not limited to, hematologic and solid tumor types such as acoustic neuroma, acute leukemia, acute lymphoblastic leukemia, acute myelogenous leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer (including estrogen-receptor positive breast cancer), bronchogenic carcinoma, Burkitt's lymphoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, gastric carcinoma, germ cell testicular cancer, gestational trophobalstic disease, glioblastoma, head and neck cancer, heavy chain disease, hemangioblastoma, hepatoma, hepatocellular cancer, hormone insensitive prostate cancer, leiomyosarcoma, liposarcoma, lung cancer (including small cell lung cancer and non-small cell lung cancer), lymphangioendothelio-sarcoma, lymphangiosarcoma, lymphoblastic leukemia, lymphoma (lymphoma, including diffuse large B-cell lymphoma, follicular lymphoma, Hodgkin's lymphoma and non-Hodgkin's lymphoma), malignancies and hyPerproliferative disorders of the bladder, breast, colon, lung, ovaries, pancreas, prostate, skin and uterus, lymphoid malignancies of T-cell or B-cell origin, leukemia, medullary carcinoma, medulloblastoma, melanoma, meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, peripheral T-cell lymphoma, pinealoma, polycythemia vera, prostate cancer (including hormone-insensitive (refractory) prostate cancer), rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), stomach cancer, squamous cell carcinoma, synovioma, sweat gland carcinoma, testicular cancer (including germ cell testicular cancer), thyroid cancer, Waldenstrom's macroglobulinemia, testicular tumors, uterine cancer, Wilms' tumor and the like.

Non-limiting examples of the cancer include acute lymphoblastic leukemia, childhood; acute myeloid leukemia/other myeloid malignancies, childhood; adrenocortical carcinoma, childhood; astrocytomas, childhood; atypical teratoid/rhabdoid tumor, childhood central nervous system; basal cell carcinoma, childhood; bladder cancer, childhood; bone, malignant fibrous histiocytoma of and osteosarcoma; brain and spinal cord tumors overview, childhood; brain stem glioma, childhood; (brain tumor), childhood astrocytomas; (brain tumor), childhood central nervous system atypical teratoid/rhabdoid tumor; (brain tumor), childhood central nervous system embryonal tumors; (brain tumor), childhood central nervous system germ cell tumors; (brain tumor), childhood craniopharyngioma; (brain tumor), childhood ependymoma; breast cancer, childhood; bronchial tumors, childhood; carcinoid tumors, childhood; carcinoma of unknown primary, childhood; cardiac (heart) tumors, childhood; central nervous system atypical teratoid/rhabdoid tumor, childhood; central nervous system embryonal tumors, childhood; central nervous system germ cell tumors, childhood; cervical cancer, childhood; chordoma, childhood; colorectal cancer, childhood; craniopharyngioma, childhood; effects, treatment for childhood cancer, late; embryonal tumors, central nervous system, childhood; ependymoma, childhood; esophageal tumors, childhood; esthesioneuroblastoma, childhood; ewing sarcoma; extracranial germ cell tumors, childhood; gastric (stomach) cancer, childhood; gastrointestinal stromal tumors, childhood; germ cell tumors, childhood central nervous system; germ cell tumors, childhood extracranial; glioma, childhood brain stem; head and neck cancer, childhood; heart tumors, childhood; hematopoietic cell transplantation, childhood; histiocytoma of bone, malignant fibrous and osteosarcoma; histiocytosis, langerhans cell; hodgkin lymphoma, childhood; kidney tumors of childhood, wilms tumor and other; langerhans cell histiocytosis; laryngeal cancer, childhood; late effects of treatment for childhood cancer; leukemia, childhood acute lymphoblastic; leukemia, childhood acute myeloid/other childhood myeloid malignancies; liver cancer, childhood; lung cancer, childhood; lymphoma, childhood Hodgkin; lymphoma, childhood non-Hodgkin; malignant fibrous histiocytoma of bone and osteosarcoma; melanoma, childhood; mesothelioma, childhood; midline tract carcinoma, childhood; multiple endocrine neoplasia, childhood; myeloid leukemia, childhood acute/other childhood myeloid malignancies; nasopharyngeal cancer, childhood; neuroblastoma, childhood; non-hodgkin lymphoma, childhood; oral cancer, childhood; osteosarcoma and malignant fibrous histiocytoma of bone; ovarian cancer, childhood; pancreatic cancer, childhood; papillomatosis, childhood; paraganglioma, childhood; pediatric supportive care; pheochromocytoma, childhood; pleuropulmonary blastoma, childhood; retinoblastoma; rhabdomyosarcoma, childhood; salivary gland cancer, childhood; sarcoma, childhood soft tissue; (sarcoma), ewing sarcoma; (sarcoma), osteosarcoma and malignant fibrous histiocytoma of bone; (sarcoma), childhood rhabdomyosarcoma; (sarcoma) childhood vascular tumors; skin cancer, childhood; spinal cord tumors overview, childhood brain and; squamous cell carcinoma (skin cancer), childhood; stomach (gastric) cancer, childhood; supportive care, pediatric; testicular cancer, childhood; thymoma and thymic carcinoma, childhood; thyroid tumors, childhood; transplantation, childhood hematopoietic; childhood carcinoma of unknown primary; unusual cancers of childhood; vaginal cancer, childhood; vascular tumors, childhood; and wilms tumor and other childhood kidney tumors.

Non-limiting examples of cancer include embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoid/rhabdoid tumor of the central nervous system, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer.

Methods for Treating Autoimmune Diseases

Some embodiments disclosed herein provide methods for treating an autoimmune disease in a human subject in need thereof, comprising (optionally) identifying a human subject having an autoimmune disease and in need of a decreased expression level of a APEX1 gene; and administering to the human subject an effective amount of a nitroxide antioxidant. In some embodiments, the methods disclosed herein may be used to treat a human subject shows no symptoms of an autoimmune disease, but is at risk of having an autoimmune disease. Exemplary risk factors for an autoimmune disease include, but are not limited to, age, family history, health conditions, medical history, habits, or a combination thereof. In some embodiments, risk factors for an autoimmune disease comprise a increased expression level of APEX1.

In some embodiments, Autoimmunity is the system of immune responses of an organism against its own healthy cells and tissues. Any disease that results from such an aberrant immune response is termed an "autoimmune disease". Prominent examples include celiac disease, diabetes mellitus type 1, sarcoidosis, systemic lupus erythematosus (SLE), Sjögren's syndrome, eosinophilic granulomatosis with polyangiitis, Hashimoto's thyroiditis, Graves' disease, idiopathic thrombocytopenic purpura, Addison's disease, rheumatoid arthritis (RA), ankylosing spondylitis, polymyositis (PM), and dermatomyositis (DM). Autoimmune diseases are very often treated with steroids In some embodiments, administering to the human subject an effective amount of the nitroxide antioxidant results in a decreased expression level of a gene, for example a gene associated with base excision repair activity. The genes associated with base excision repair encode proteins that can be DNA glycosylases, AP endonucleases, DNA polymerases, Flap endonucleases, DNA ligases, MBD4, NEIL1, or a homologue thereof. The treatment of the human subject with the effective amount of the nitroxide antioxidant results in a decreased expression level of the gene. For example, the treatment results in a decreased expression level of APEX1. The decreased expression levels of APEX1, improves base excision repair function and endodeoxyribonuclease activity resulting in a decrease in or disappearance of signs and symptoms of the autoimmune disease, including the curing of the autoimmune disease. In some embodiments, the decreased expression level of APEX1, improves base excision repair function. The improved base excision repair function results in a decrease in or disappearance of signs and symptoms of the autoimmune disease, including the curing of the autoimmune disease.

Non-limiting examples of autoimmune diseases include rheumatoid arthritis, osteoarthritis, juvenile chronic arthritis, septic arthritis, Lyme arthritis, psoriatic arthritis, reactive arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis scleroderma, graft versus host disease, organ transplant rejection, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpurea, microscopic vasculitis of the kidneys, chronic active hepatitis, uveitis, septic shock, toxic shock syndrome, sepsis syndrome, cachexia, infectious diseases, parasitic diseases, acquired immunodeficiency syndrome, acute transverse myelitis, Huntington's chorea, Parkinson's disease, Alzheimer's disease, stroke, primary biliary cirrhosis, hemolytic anemia, malignancies, heart failure, myocardial infarction, Addison's disease, sporadic, polyglandular deficiency type I and polyglandular deficiency type II, Schmidt's syndrome, adult (acute) respiratory distress syndrome, alopecia, alopecia greata, seronegative arthopathy, arthropathy, Reiter's disease, psoriatic arthropathy, ulcerative colitic arthropathy, enteropathic synovitis, *Chlamydia, Yersinia* and *Salmonella* associated arthropathy, spondyloarthopathy, atheromatous disease/arteriosclerosis, atopic allergy, autoimmune bullous disease, *Pemphigus vulgaris, Pemphigus foliaceus*, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis B, Hepatitis C, common varied immunodeficiency (common variable hypogammaglobulinaemia), dilated cardiomyopathy, female infertility, ovarian failure, premature ovarian failure, fibrotic lung disease, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjogren's disease associated lung disease, ankylosing spondylitis associated lung disease, vasculitic diffuse lung disease, haemosiderosis associated lung disease, drug-induced interstitial lung disease, fibrosis, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis nigricans, hypoparathyroidism, acute immune disease associated with organ transplantation, chronic immune disease associated with organ transplantation, osteoarthrosis, primary sclerosing cholangitis, psoriasis type 1, psoriasis type 2, idiopathic leucopaenia, autoimmune neutropaenia, renal disease NOS, glomerulonephritides, microscopic vasulitis of the kidneys, lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Sjogren's syndrome, Takayasu's disease/arteritis, autoimmune thrombocytopaenia, idiopathic thrombocytopaenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo acute liver disease, chronic liver diseases, alcoholic cirrhosis, alcohol-induced liver injury, choleosatatis, idiosyncratic liver disease, Drug-Induced hepatitis, Non-alcoholic Steatohepatitis, allergy and asthma, group B streptococci (GB S) infection, mental disorders (e.g., depression and schizophrenia), Th2 Type and Th1 Type mediated diseases, acute and chronic pain (different forms of pain), and cancers such as lung, breast, stomach, bladder, colon, pancreas, ovarian, prostate and rectal cancer and hematopoietic malignancies (leukemia and lymphoma). The human antibodies, and antibody portions of the present application can be used to treat humans suffering from autoimmune diseases, in particular those associated with inflammation, including, rheumatoid spondylitis, allergy, autoimmune diabetes, autoimmune uveitis.

Non-limiting examples of autoimmune diseases include acquired immunodeficiency disease syndrome (AIDS), autoimmune lymphoproliferative syndrome, hemolytic anemia, inflammatory diseases, and thrombocytopenia, acute or chronic immune disease associated with organ transplantation, Addison's disease, allergic diseases, alopecia, alopecia areata, atheromatous disease/arteriosclerosis, atherosclerosis, arthritis (including osteoarthritis, juvenile chronic arthritis, septic arthritis, Lyme arthritis, psoriatic arthritis and reactive arthritis), autoimmune bullous disease, abetalipoprotemia, acquired immunodeficiency-related diseases, acute immune disease associated with organ transplantation, acquired acrocyanosis, acute and chronic parasitic or infectious processes, acute pancreatitis, acute renal failure, acute rheumatic fever, acute transverse myelitis, adenocarcinomas, aerial ectopic beats, adult (acute) respiratory distress syndrome, AIDS dementia complex, alcoholic cirrhosis, alcohol-induced liver injury, alcohol-induced hepatitis, allergic conjunctivitis, allergic contact dermatitis, allergic rhinitis, allergy and asthma, allograft rejection, alpha-1-antitrypsin deficiency, Alzheimer's disease, amyotrophic lateral sclerosis, anemia, angina pectoris, ankylosing spondylitis associated lung disease, anterior horn cell degeneration, antibody mediated cytotoxicity, antiphospholipid syndrome, anti-receptor hypersensitivity reactions, aortic and peripheral aneurysms, aortic dissection, arterial hypertension, arteriosclerosis, arteriovenous fistula, arthropathy, asthenia, asthma, ataxia, atopic allergy, atrial fibrillation (sustained or paroxysmal), atrial flutter, atrioventricular block, atrophic autoimmune hypothyroidism, autoimmune haemolytic anaemia, autoimmune hepatitis, type-1 autoimmune hepatitis (classical autoimmune or lupoid hepatitis), autoimmune mediated hypoglycaemia, autoimmune neutropaenia, autoimmune thrombocytopaenia, autoimmune thyroid disease, B cell lymphoma, bone graft rejection, bone marrow transplant (BMT) rejection, bronchiolitis obliterans, bundle branch block, burns, cachexia, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, *Chlamydia*, choleosatatis, chronic alcoholism, chronic active hepatitis, chronic fatigue syndrome, chronic immune disease associated with organ transplantation, chronic eosinophilic pneumonia, chronic inflammatory pathologies, chronic mucocutaneous candidiasis, chronic obstructive pulmonary disease (COPD), chronic salicylate intoxication, colorectal common varied immunodeficiency (common variable hypogammaglobulinaemia), conjunctivitis, connective tissue disease associated interstitial lung disease, contact dermatitis, Coombs positive haemolytic anaemia, cor pulmonale, Creutzfeldt-Jakob disease, cryptogenic autoimmune hepatitis, cryptogenic fibrosing alveolitis, culture negative sepsis, cystic fibrosis, cytokine therapy associated disorders, Crohn's disease, dementia pugilistica, demyelinating diseases, dengue hemorrhagic fever, dermatitis, dermatitis scleroderma, dermatologic conditions, dermatomyositis/polymyositis associated lung disease, diabetes, diabetic arteriosclerotic disease, diabetes mellitus, Diffuse Lewy body disease, dilated cardiomyopathy, dilated congestive cardiomyopathy, discoid lupus erythematosus, disorders of the basal ganglia, disseminated intravascular coagulation, Down's Syndrome in middle age, drug-induced interstitial lung disease, drug-induced hepatitis, drug-induced movement disorders induced by drugs which block CNS dopamine, receptors, drug sensitivity, eczema, encephalomyelitis, endocarditis, endocrinopathy, enteropathic synovitis, epiglottitis, Epstein-Barr virus infection, erythromelalgia, extrapyramidal and cerebellar disorders, familial hematophagocytic lymphohistiocytosis, fetal thymus implant rejection, Friedreich's ataxia, functional peripheral arterial disorders, female infertility, fibrosis, fibrotic lung disease, fungal sepsis, gas gangrene, gastric ulcer, giant cell arteritis, glomerular nephritis, glomerulonephritides, Goodpasture's syndrome, goitrous autoimmune hypothyroidism (Hashimoto's disease), gouty arthritis, graft rejection of any organ or tissue, graft versus host disease, gram negative sepsis, gram positive sepsis, granulomas due to intracellular organisms, group B streptococci (GBS) infection, Grave's disease, haemosiderosis associated lung disease, hairy cell leukemia, hairy cell leukemia, Hallerrorden-Spatz disease, Hashimoto's thyroiditis, hay fever, heart transplant rejection, hemachromatosis, hematopoietic malignancies (leukemia and lymphoma), hemolytic anemia, hemolytic uremic syndrome/thrombolytic thrombocytopenic purpura, hemorrhage, Henoch-Schoenlein purpurea, Hepatitis A, Hepatitis B, Hepatitis C, HIV infection/HIV neuropathy, Hodgkin's disease, hypoparathyroidism, Huntington's chorea, hyperkinetic movement disorders, hypersensitivity reactions, hypersensitivity pneumonitis, hyperthyroidism, hypokinetic movement disorders, hypothalamic-pituitary-adrenal axis evaluation, idiopathic Addison's disease, idiopathic leucopaenia, idiopathic pulmonary fibrosis, idiopathic thrombocytopaenia, idiosyncratic liver disease, infantile spinal muscular atrophy, infectious diseases, inflammation of the aorta, inflammatory bowel disease, insulin dependent diabetes mellitus, interstitial pneumonitis, iridocyclitis/uveitis/optic neuritis, ischemia-reperfusion injury, ischemic stroke, juvenile pernicious anaemia, juvenile rheumatoid arthritis, juvenile spinal muscular atrophy, Kaposi's sarcoma, Kawasaki's disease, kidney transplant rejection, *Legionella*, leishmaniasis, leprosy, lesions of the corticospinal system, linear IgA disease, lipidema, liver transplant rejection, Lyme disease, lymphederma, lymphocytic infiltrative lung disease, malaria, male infertility idiopathic or NOS, malignant histiocytosis, malignant melanoma, meningitis, meningococcemia, microscopic vasculitis of the kidneys, migraine headache, mitochondrial multisystem disorder, mixed connective tissue disease, mixed connective tissue disease associated lung disease, monoclonal gammopathy, multiple myeloma, multiple systems degenerations (Mencel Dejerine-Thomas Shi-Drager and Machado-Joseph), myalgic encephalitis/Royal Free Disease, myasthenia gravis, microscopic vasculitis of the kidneys, *Mycobacterium avium intracellulare, Mycobacterium tuberculosis*, myelodyplastic syndrome, myocardial infarction, myocardial ischemic disorders, nasopharyngeal carcinoma, neonatal chronic lung disease, nephritis, nephrosis, nephrotic syndrome, neurodegenerative diseases, neurogenic I muscular atrophies, neutropenic fever, Non-alcoholic Steatohepatitis, occlusion of the abdominal aorta and its branches, occlusive arterial disorders, organ transplant rejection, orchitis/epidydimitis, orchitis/vasectomy reversal procedures, organomegaly, osteoarthrosis, osteoporosis, ovarian failure, pancreas transplant rejection, parasitic diseases, parathyroid transplant rejection, Parkinson's disease, pelvic inflammatory disease, *Pemphigus vulgaris, Pemphigus foliaceus*, pemphigoid, perennial rhinitis, pericardial disease, peripheral atherlosclerotic disease, peripheral vascular disorders, peritonitis, pernicious anemia, phacogenic uveitis, *Pneumocystis carinii* pneumonia, pneumonia, POEMS syndrome (polyneuropathy, organomegaly, endocrinopathy, monoclonal gammopathy, and skin changes syndrome), post perfusion syndrome, post pump syndrome, post-MI cardiotomy syndrome, postinfectious interstitial lung disease, premature ovarian failure, primary biliary cirrhosis, primary sclerosing hepatitis, primary myxoedema, primary pulmonary hypertension, primary sclerosing cholangitis, primary vasculitis, Progressive supranucleo Palsy, psoriasis, psoriasis type 1, psoriasis type 2, psoriatic arthropathy, pulmonary hypertension secondary to connective tissue disease, pulmonary manifestation of polyarteritis nodosa, post-inflammatory interstitial lung disease, radiation fibrosis, radiation therapy, Raynaud's phenomenon and disease, Raynoud's disease, Refsum's disease, regular narrow QRS tachycardia, Reiter's disease, renal disease NOS, renovascular hypertension, reperfusion injury, restrictive cardiomyopathy, rheumatoid arthritis associated interstitial lung disease, rheumatoid spondylitis, sarcoidosis, Schmidt's syndrome, scleroderma, senile chorea, Senile Dementia of Lewy body type, sepsis syndrome, septic shock, seronegative arthropathies, shock, sickle cell anemia, Sjögren's disease associated lung disease, Sjörgren's syndrome, skin allograft rejection, skin changes syndrome, small bowel transplant rejection, sperm autoimmunity, multiple sclerosis (all subtypes), spinal ataxia, spinocerebellar degenerations, spondyloarthropathy, spondyloarthopathy, sporadic, polyglandular deficiency type I sporadic, polyglandular deficiency type II, Still's disease, streptococcal myositis, stroke, structural lesions of the cerebellum, Subacute sclerosing panencephalitis, sympathetic ophthalmia, Syncope, syphilis of the cardiovascular system, systemic anaphylaxis, systemic inflammatory response syndrome, systemic onset juvenile rheumatoid arthritis, systemic lupus erythematosus, systemic lupus erythematosus-associated lung disease, systemic sclerosis, systemic sclerosis-associated interstitial lung disease, T-cell or FAB ALL, Takayasu's disease/arteritis, Telangiectasia, Th2 Type and Th1 Type mediated diseases, thromboangitis obliterans, thrombocytopenia, thyroiditis, toxicity, toxic shock syndrome, transplants, trauma/hemorrhage, type-2 autoimmune hepatitis (anti-LKM antibody hepatitis), type B insulin resistance with acanthosis nigricans, type III hypersensitivity reactions, type IV hypersensitivity, ulcerative colitic arthropathy, ulcerative colitis, unstable angina, uremia, urosepsis, urticaria, uveitis, valvular heart diseases, varicose veins, vasculitis, vasculitic diffuse lung disease, venous diseases, venous thrombosis, ventricular fibrillation, vitiligo acute liver disease, viral and fungal infections, vital encephalitis/aseptic meningitis, vital-associated hemaphagocytic syndrome, Wegener's granulomatosis, Wernicke-Korsakoff syndrome, Wilson's disease, xenograft rejection of any organ or tissue, *Yersinia* and *Salmonella*-associated arthropathy and the like.

Nitroxide Antioxidant

Nitroxide antioxidants describes a group of stable organic molecules, containing the nitroxyl group >N—O. with an unpaired electron. They have a low molecular weight, are non-toxic, do not elicit immunogenic effects on cells and easily diffuse through cell membranes. Their biological activity as antioxidants is related to the regulation of redox state in the cells. Nitroxides can undergo cyclic oxidation or reduction reactions. Their antioxidant activity is related to several mechanisms such as the direct scavenging of free radicals, transition metal ion oxidation. In addition, nitroxides exhibit superoxide dismutase (SOD)-like activity, modulate its catalase-like activity and ferroxidase-like activity, and are the inhibitors of free radical reactions such as lipid peroxidation. Nitroxides have dynamic beneficial impact on all cellular processes from inhibition of oxidative stress and reducing inflammation, while under certain conditions they may also lead to its intensification, for example, in tumor cells. The different beneficial impact on cellular processes provides each cell with necessary support to prevent or reverse diseases and conditions through optimizing cellular activity and associated biological processes in a healthy state and promoting cell death in diseases such as cancer.

Cyclic nitroxides, also known as aminoxyls or nitroxyls, are stable free radicals stabilized by methyl groups at the a position in five-membered pyrrolidine, pyrroline or oxazolidine and six-membered piperidine ring structures. The methyl groups confer stability to the nitroxide radicals by preventing radical-radical dismutation and also limit access to reactive substances, which can quench the radical species. The substituent groups on the ring (denoted by R—) produce a diverse range of compounds that can be directed to specific hydrophilic or hydrophobic regions in the cellular microenvironment. The redox transformations between the oxidation states of nitroxide, hydroxylamine and the oxoammonium cation acts as an efficient redox couple, which can support catalytic processes via reversible electron redox reactions. (Soule, Benjamin P et al. "The chemistry and biology of nitroxide compounds." Free radical biology & medicine vol. 42,11 (2007): 1632-50. doi:10.1016/j.freeradbiomed.2007.02.030).

The mechanism of action exerted by nitroxide antioxidants is very unique. In particular, nitroxide antioxidant function is characterized by a catalytic mechanism of action associated with a single-electron redox cycle. Their reduction results in the generation of hydroxylamine and oxidation in oxoammonium ion; meanwhile both reactions are reversible and repetitive such that the ratio of free radicals suppressed by nitroxide antioxidants is significantly higher than natural antioxidant processes within a cell. Hydroxylamine also exhibits antioxidant properties because it is easily oxidized to nitroxide. As mentioned above, the nitroxides devoid of electrical charge easily diffuse through the cell membranes, thus they can also inactivate the reactive oxygen species formed in the cells and modulate the concentration of intracellular nitric oxide. Their molecular structure and composition make nitroxide antioxidants additionally efficacious in tissues that prevent transport of different molecules, such as neuronal tissue across the blood brain barrier.

Non-limiting examples of the nitroxide antioxidant include 2-ethyl-2,5,5-trimethyl-3-oxazolidine-1-oxyl (OXANO), 2,2,6,6-tetramethylpiperidine-1-oxyl (TEMPO), 4-hydroxy-2,2,6,6-tetramethylpiperidine-1-oxyl (TEMPOL), 4-amino-2,2,6,6-tetramethyl-1-piperidinyloxy (Tempamine), 3-Amin omethyl-PROXYL, 3-Cyano-PROXYL, 3-Carbamoyl-PROXYL, 3-Carboxy-PROXYL, and 4-Oxo-TEMPO. TEMPO can also be substituted, typically in the 4 position, for example, 4-amino, 4-(2-bromoacetamido), 4-(ethoxyfluorophosphonyloxy), 4-hydroxy, 4-(2-iodoacetamido), 4-isothiocyanato, 4-maleimido, 4-(4-nitrobenzoyloxyl), 4-phosphonooxy, 2,2,6,6-tetramethyl-4-oxo-1-piperidinyloxy (TEMPONE), 1-Hydroxy-2,2,6,6-tetramethyl-4-oxo-piperidine.HCl (TEMPONE-H), 1,2-dipalmitoyl-sn-glycero-3-phospho(tempo)choline (TEMPO PC), (4-[N,N-dimethyl-N-(2-hydroxyethyl)]ammonium-2,2,6,6-tetramethylpiperidine-1-oxyl (TEMPO Choline), and the like.

The use of other nitroxide compounds is also contemplated. Nitroxide stable radicals demonstrate effective antioxidative activity in various biological systems ranging from molecular, cellular, and laboratory animal level. Nitroxides have been reported to catalyze O2. dismutation through two different catalytic pathways including reductive and oxidative reaction mechanisms. Conversely, kinetics analysis of rapid mixing stopped flow experiments de-signed to measure the effect of nitroxides on superoxide decay did not reveal any SOD activity, leading to the conclusion that nitroxides act as free radical scavengers.

Studies have shown that unlike other antioxidants, nitroxides are characterized by a catalytic mechanism of action associated with a single-electron redox cycle. Their reduction results in the generation of hydroxylamine and oxidation in oxoammonium ion; meanwhile both reactions are reversible. Hydroxylamine also exhibits antioxidant properties because it is easily oxidized to nitroxide. Nitroxide antioxidants undergo redox cycles. They are easily reduced to hydroxylamines and oxidized to oxoammonium salts.

According to certain embodiments the nitroxide compound can be selected from the following formulas:

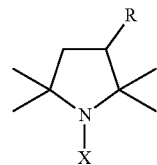

wherein X is selected from O and OH, and R is selected from COOH, CONH, CN, and CH2NH2;

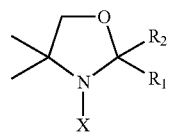

wherein X is selected from O and OH, and R1 is selected from CH3 and spirocyclohexyl, and R2 is selected from C2H5 and spirocyclohexyl;

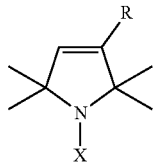

wherein X is selected from O and OH and R is selected from CONH; and

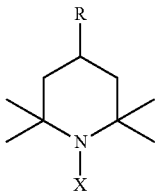

wherein X is selected from O and OH and R is selected from H, OH, and NH2.

Suitable nitroxide compounds can also be found in Proctor, U.S. Pat. No. 5,352,442, and Mitchell et al., U.S. Pat. No. 5,462,946, both of which are hereby incorporated by reference in their entireties.

In some embodiments, the nitroxide antioxidant has a general formula:

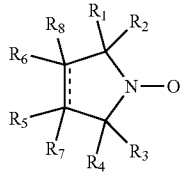

wherein the dashed line denotes a saturated bond or an unsaturated bond, wherein when the dashed line denotes an unsaturated bond, R7 and R8 are absent; R1-R4 are each independently a C1-4-alkyl, or alternatively, R1 and R2, and/or R3 and R4, together form a 3-7-membered alicyclic ring; and R5-R8 are each independently selected from the group consisting of hydrogen, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, sulfonate, sulfate, cyano, nitro, azide, phosphonyl, phosphinyl, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, hydrazine, and amino, In some embodiments, the nitroxide antioxidant includes or is associated with (e.g., binds to or is conjugated with) a bioeffector molecule. For example, the bioeffector molecule is a targeting subunit bound to the nitroxide antioxidant, such as a mitochondrial targeting subunit. A targeting subunit can direct activity of the nitroxide antioxidant to a predetermined location within or on the cell. Non-limiting examples of mitochondrial targeting bioeffector molecules includes triphenylphosphine (TPP), gramicidin, and any functional group effectively charged to be attracted to the polarized mitochondria.

In some embodiments, the nitroxide antioxidant is structurally cyclic having a ring structure including a nitroxide molecule incorporated therein. In some embodiments, the nitroxide antioxidant is characterized as the nitroxide molecule functioning as the catalytic center.

Dosage

In some embodiments, the nitroxide antioxidant, non-toxic salts thereof, acid addition salts thereof or hydrates thereof may be administered systemically or locally, usually by oral or parenteral administration. The doses to be administered can be determined depending upon, for example, age, body weight, symptom, the desired therapeutic effect, the route of administration, and the duration of the treatment. In the human adult, the dose per person at a time can be generally from about 0.01 to about 4000 mg, by oral administration, up to several times per day. Specific examples of particular amounts contemplated via oral administration include about 0.02, 0.03, 0.04, 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, 1000 or more mg. The dose per person at a time can be generally from about 0.01 to about 300 mg/kg via parenteral administration (preferably intravenous administration), from one to four or more times per day. Specific examples of particular amounts contemplated include about 0.02, 0.03, 0.04, 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1, 2, 3, 4, 5, 6, 7, 8, 9, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300 or more mg/kg. Continuous intravenous administration can also contemplated for from 1 to 24 hours per day to achieve a target concentration from about 0.01 mg/L to about 100 mg/L. Non-limiting examples of particular amounts contemplated via this route include about 0.02, 0.03, 0.04, 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more mg/L. The dose to be used does can depend upon various conditions, and there may be cases wherein doses lower than or greater than the ranges specified above are used.

Compositions

The nitroxide antioxidant can be administered in the form of, for example, solid compositions, liquid compositions or other compositions for oral administration, injections, liniments or suppositories for parenteral administration.

Solid compositions for oral administration include compressed tablets, pills, capsules, dispersible powders and granules. Capsules include hard capsules and soft capsules. In such solid compositions, Tempol may be admixed with an excipient (e.g. lactose, mannitol, glucose, microcrystalline cellulose, starch), combining agents (hydroxypropyl cellulose, polyvinyl pyrrolidone or magnesium metasilicate aluminate), disintegrating agents (e.g. cellulose calcium glycolate), lubricating agents (e.g. magnesium stearate), stabilizing agents, agents to assist dissolution (e.g. glutamic acid or aspartic acid), or the like. The agents may, if desired, be coated with coating agents (e.g. sugar, gelatin, hydroxypropyl cellulose or hydroxypropylmethyl cellulose phthalate), or be coated with two or more films. Further, coating may include containment within capsules of absorbable materials such as gelatin.

Liquid compositions for oral administration include pharmaceutically acceptable solutions, suspensions, emulsions, syrups and elixirs. In such compositions, the nitroxide antioxidant is dissolved, suspended or emulsified in a commonly used diluent (e.g. purified water, ethanol or mixture thereof). Furthermore, such liquid compositions may also comprise wetting agents or suspending agents, emulsifying agents, sweetening agents, flavoring agents, perfuming agents, preserving agents, buffer agents, or the like.

Injections for parenteral administration include solutions, suspensions, emulsions and solids which are dissolved or suspended. For injections, the nitroxide antioxidant can be dissolved, suspended and emulsified in a solvent. The solvents include, for example, distilled water for injection, physiological salt solution, vegetable oil, propylene glycol, polyethylene glycol, alcohol such as ethanol, or a mixture thereof. Moreover the injections can also include stabilizing agents, agents to assist dissolution (e.g. glutamic acid, aspartic acid or POLYSORBATE80™), suspending agents, emulsifying agents, soothing agents, buffer agents, preserving agents, etc. They can be sterilized in the final process or manufactured and prepared by sterile procedure. They can also be manufactured in the form of sterile solid compositions, such as a freeze-dried composition, and they may be sterilized or dissolved immediately before use in sterile distilled water for injection or some other solvent.

Other compositions for parenteral administration include liquids for external use, and ointment, endermic liniments, inhale, spray, suppositories for rectal administration and pessaries for vaginal administration which comprise the nitroxide antioxidant and are administered by methods known in the art.

Spray compositions can comprise additional substances other than diluents: e.g. stabilizing agents (e.g. sodium sulfite hydride), isotonic buffers (e.g. sodium chloride, sodium citrate or citric acid). A small aerosol particle size useful for effective distribution of the medicament can be obtained by employing self-propelling compositions containing the drugs in micronized form dispersed in a propellant composition. Effective dispersion of the finely divided drug particles can be accomplished with the use of very small quantities of a suspending agent, present as a coating on the micronized drug particles. Evaporation of the propellant from the aerosol particles after spraying from the aerosol container leaves finely divided drug particles coated with a fine film of the suspending agent. In the micronized form, the average particle size can be less than about 5 microns. The propellant composition may employ, as the suspending agent, a fatty alcohol such as oleyl alcohol. The minimum quantity of suspending agent can be approximately 0.1 to 0.2 percent by weight of the total composition. The amount of suspending agent can be less than about 4 percent by weight of the total composition to maintain an upper particle size limit of less than 10 microns or 5 microns. Propellants that may be employed include hydrofluoroalkane propellants and chlorofluorocarbon propellants. Dry powder inhalation may also be employed.

EXAMPLES

Some aspects of the embodiments discussed above are disclosed in further detail in the following examples, which are not in any way intended to limit the scope of the present disclosure.

In order to facilitate understanding, the specific embodiments are provided to help interpret the technical proposal, that is, these embodiments are only for illustrative purposes, but not in any way to limit the scope of the invention. Unless otherwise specified, embodiments do not indicate the specific conditions, are in accordance with the conventional conditions or the manufacturer's recommended conditions.

Example 1. Effects of Tempol on Expression of Genes Associated with Base Excision Repair Activity To assess the effects of Tempol on gene expression, Tempol was administered to experimental mice at a dose of 5 mg/g of food from 14 months to 31 months after birth. Mice receiving the same food without the addition of Tempol were used as a negative control. At the age of 31 months, the experimental animals were sacrificed and the hearts were surgically removed. The expression of a broad spectrum of genes in the cardiac tissue was assessed using chip-based microarray technology. Such chips are well known in the art and are widely used to assess gene expression. The experimental results showed that APEX1 exhibited statistically significant decrease in expression. This result is shown in Table 1.

| Symbol | Gene title | Fold change |
|--------|------------|-------------|
| APEX1 | Apurinic/apyrimidinic endodeoxyribonuclease 1 | −1.23 |

Example 2. Treating Age-Related Increase in Gene Expression

A 70-kilogram human subject over the age of 65 is identified as having, or known to have, or suspected of having an increased expression level of APEX1. The human subject is administered a dose of 2000 mg of Tempol (or another nitroxide antioxidant) per day for 180 days. This may be administered in a single dose, or may be administered as a number of smaller doses over a 24-hour period: for example, four 500-mg doses at eight-hour intervals. Following treatment, the serum level of APEX1, is decreased.

Example 3. Treating a Human Subject with Increased Gene Expression

A 70-kilogram human subject is identified as having, or known to have, or suspected of having an increased expression level of APEX1. The human subject is administered a dose of 2000 mg of Tempol (or another nitroxide antioxidant) per day for 180 days. This may be administered in a single dose, or may be administered as a number of smaller doses over a 24-hour period: for example, four 500-mg doses at eight-hour intervals. Following treatment, the serum level of APEX1, is decreased.

Example 4. Treating a Human Subject with an Age-Related Disease

A 70-kilogram human subject over the age of 65 and having a cardiovascular disease is identified for an increased expression level of APEX1. Or a 70-kilogram human subject over the age of 65 is known to have a cardiovascular disease and/or increased expression level of APEX1. The human subject is administered a dose of 2000 mg of Tempol (or another nitroxide antioxidant) per day for 180 days. This may be administered in a single dose, or may be administered as a number of smaller doses over a 24-hour period: for example, four 500-mg doses at eight-hour intervals. Following treatment, the serum level of APEX1, is decreased.

Example 5. Treating a Human Subject at Risk of Developing Cancer

A 70-kilogram human subject at risk of developing colorectal cancer is identified for increased expression level of APEX1. Or a 70-kilogram human subject is known to be at risk of developing colorectal cancer and/or have increased expression level of APEX1. The human subject is administered a dose of 2000 mg of Tempol (or another nitroxide antioxidant) per day for 180 days. This may be administered in a single dose, or may be administered as a number of smaller doses over a 24-hour period: for example, four 500-mg doses at eight-hour intervals. Following treatment, the serum level of APEX1, is decreased.

Example 6. Treating a Human Subject at Risk of Developing an Autoimmune Disease A 70-kilogram human subject at risk of developing an autoimmune disease (e.g., rheumatoid arthritis) is identified for increased expression level of APEX1. Or a 70-kilogram human subject is known to be at risk of developing an autoimmune disease and/or have increased expression level of APEX1. The human subject is administered a dose of 2000 mg of Tempol (or another nitroxide antioxidant) per day for 180 days. This may be administered in a single dose, or may be administered as a number of smaller doses over a 24-hour period: for example, four 500-mg doses at eight-hour intervals. Following treatment, the serum level of APEX1, is decreased.

Example 7. Treating a Human Subject at Risk of Developing a Condition Due to Aging A 70-kilogram human subject of 45 years old at risk of developing a condition due to aging is identified. Or a 70-kilogram human subject of 45 years old is known to be at risk of developing a condition. The human subject is administered a dose of 2000 mg of Tempol (or another nitroxide antioxidant) per day for 180 days. This may be administered in a single dose, or may be administered as a number of smaller doses over a 24-hour period: for example, four 500-mg doses at eight-hour intervals. Following treatment, the serum level of APEX1, is decreased.

Example 8. Treating a Human Subject at Risk of Developing a Neurodegenerative Disease A 70-kilogram human subject at risk of developing a neurodegenerative disease (e.g., Parkinson's Disease) is identified for increased expression level of APEX1. Or a 70-kilogram human subject is known to be at risk of developing a neurodegenerative disease and/or have increased expression level of APEX1. The human subject is administered a dose of 2000 mg of Tempol (or another nitroxide antioxidant) per day for 180 days. This may be administered in a single dose, or may be administered as a number of smaller doses over a 24-hour period: for example, four 500-mg doses at eight-hour intervals. Following treatment, the serum level of APEX1, is decreased.

Example 9. Treating a Human Subject Having an Infection

A 70-kilogram human subject having an infection (e.g., a bacterial, fungal, or viral infection) is identified for increased expression level of APEX1. Or a 70-kilogram human subject is known to have an infection and/or have increased expression level of APEX1. The human subject is administered a dose of 2000 mg of Tempol (or another nitroxide antioxidant) per day for 180 days. This may be administered in a single dose, or may be administered as a number of smaller doses over a 24-hour period: for example, four 500-mg doses at eight-hour intervals. Following treatment, the serum level of APEX1, is decreased.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of decreasing expression level of a gene encoding APEX1, the method comprising:
   identifying a subject having a disease or condition associated with increased expression level of the gene encoding APEX1, wherein the disease or condition is selected from the group consisting of cancer, an ocular neovascular disease, resistance to one or more chemotherapeutic agents, atherosclerosis, and a disease or condition which is not cancer, ocular neovascular disease, or coronary artery disease, wherein the disease or condition which is not cancer, ocular neovascular disease, or coronary artery disease is selected from the group consisting of Osteogenesis imperfecta, Spondyloepiphyseal dysplasia, Spondyloepimetaphyseal dysplasia, Achondrogenesis, hypochondrogenesis, Kniest dysplasia, Stickler syndrome, Ehlers-Danlos syndrome, Familial porencephaly, Hereditary angiopathy with nephropathy, aneurysms and muscle cramps syndrome, Benign familial haematuria, Alport syndrome, Leiomyomatosis, Bethlem myopathy, Ullrich congenital muscular dystrophy, Dystrophic epidermolysis bullosa, Corneal endothelial dystrophies Multiple epiphyseal dysplasia, Autosomal recessive Stickler syndrome, Schmid metaphyseal chondrodysplasia, Marshall syndrome, Otospondylomegaepiphyseal dysplasia Deafness, and Junctional epidermolysis bullosaother Knobloch syndrome; and
   administering an effective amount of a nitroxide antioxidant to the subject,
   wherein the nitroxide antioxidant is 4-hydroxy-2,2,6,6-tetramethylpiperidine-1-oxyl (TEMPOL), and
   whereby the expression level of the gene encoding APEX1 is decreased.

2. The method of claim 1, wherein the disease or condition is cancer.

3. The method of claim 1, wherein the disease or condition is an ocular neovascular disease.

4. The method of claim 1, wherein decreased expression of APEX1 prevents coronary artery disease.

5. The method of claim 1, wherein the disease or condition is resistance to one or more chemotherapeutic agents.

6. The method of claim 1, wherein the disease or condition is atherosclerosis.

7. The method of claim 1, wherein the decreased expression of APEX1 inhibits tumor growth.

8. The method of claim 1, wherein the disease or condition is caused by increased APEX1 activity.

9. The method of claim 1, wherein the decreased expression level of APEX1 activates NRF2.

10. The method of claim 1, wherein the expression level of the gene encoding APEX1 is decreased in cardiac tissue of the subject.

11. The method of claim 10, wherein the expression level of the gene encoding APEX1 is decreased 1.23 fold.

* * * * *

UNITED STATES PATENT AND TRADEMARK OFFICE
CERTIFICATE OF CORRECTION

PATENT NO. : 11,510,913 B1
APPLICATION NO. : 17/330182
DATED : November 29, 2022
INVENTOR(S) : Louis Habash It is certified that error appears in the above-identified patent and that said Letters Patent is hereby corrected as shown below:

On the Title Page

Column 2 (item (56) Other Publications), Line 1, delete "("Astable" and insert -- ("A stable --.

In the Specification

Column 13, Line 10, delete "The a" and insert -- The --.

Column 13, Line 47, delete "glycolysases" and insert -- glycosylases --.

Column 16, Line 52, delete "APEL." and insert -- APE1. --.

Column 18, Line 3, delete "NEILL." and insert -- NEIL1. --.

Column 18, Line 46, delete "syndrome" and insert -- syndrome. --.

Column 22, Line 49, delete "trophobalstic" and insert -- trophoblastic --.

Column 22, Line 58, delete "hyPerproliferative" and insert -- hyperproliferative --.

Column 24, Line 24, delete "psteosarcoma," and insert -- osteosarcoma, --.

Column 24, Line 54, delete "steroids" and insert -- steroids. --.

Column 25, Line 21, delete "Henoch-Schoenlein purpurea," and insert -- Henoch-Schonlein purpura, --.

Column 25, Line 31, delete "greata," and insert -- areata, --.

Column 25, Line 32, delete "arthopathy," and insert -- arthropathy, --.

Signed and Sealed this
Twenty-third Day of May, 2023

Katherine Kelly Vidal
*Director of the United States Patent and Trademark Office*

Column 25, Line 34, delete "Chlamydia, Yersinia and Salmonella" and insert -- chlamydia, yersinia and salmonella --.

Column 25, Line 35, delete "spondyloarthopathy," and insert -- spondyloarthropathy, --.

Column 25, Line 37, delete "Pemphigus" and insert -- pemphigus --.

Column 25, Line 37, delete "Pemphigus" and insert -- pemphigus --.

Column 25, Line 40, delete "encephalitis" and insert -- encephalomyelitis --.

Column 25, Line 58, delete "haemosiderosis" and insert -- hemosiderosis --.

Column 26, Line 4, delete "leucopaenia," and insert -- leukopenia, --.

Column 26, Line 4, delete "neutropaenia," and insert -- neutropenia, --.

Column 26, Line 5, delete "glomerulonephritides," and insert -- glomerulonephritis, --.

Column 26, Line 5, delete "vasulitis" and insert -- vasculitis --.

Column 26, Line 20, delete "choleosatatis," and insert -- cholestasis, --.

Column 26, Line 42-43, delete "abetalipoprotemia," and insert -- abetalipoproteinemia, --.

Column 26, Line 65-66, delete "neutropaenia," and insert -- neutropenia, --.

Column 27, Line 7, delete "Chlamydia," and insert -- chlamydia, --.

Column 27, Line 7-8, delete "choleosatatis," and insert -- cholestasis, --.

Column 27, Line 39-40, delete "glomerulonephritides," and insert -- glomerulonephritis, --.

Column 27, Line 45, delete "haemosiderosis" and insert -- hemosiderosis --.

Column 27, Line 46-47, delete "Hallerrorden" and insert -- Hallervorden --.

Column 27, Line 48, delete "hemachromatosis," and insert -- hemochromatosis, --.

Column 27, Line 51, delete "Henoch-Schoenlein purpurea," and insert -- Henoch-Schonlein purpura, --.

Column 27, Line 58, delete "leucopaenia," and insert -- leukopenia, --.

Column 27, Line 67, delete "Legionella," and insert -- legionella, --.

Column 28, Line 2, delete "lipidema," and insert -- lipedema, --.

Column 28, Line 11, delete "encephalitis" and insert -- encephalomyelitis --.

Column 28, Line 13, delete "Mycobacterium" and insert -- mycobacterium --.

Column 28, Line 13, delete "Mycobacterium" and insert -- mycobacterium --.

Column 28, Line 14, delete "myelodyplastic" and insert -- myelodysplastic --.

Column 28, Line 21, delete "epidydimitis," and insert -- epididymitis, --.

Column 28, Line 25, delete "Pemphigus" and insert -- pemphigus --.

Column 28, Line 25, delete "Pemphigus" and insert -- pemphigus --.

Column 28, Line 29, delete "Pneumocystis" and insert -- pneumocystis --.

Column 28, Line 37, delete "supranucleo" and insert -- supranuclear --.

Column 28, Line 55, delete "spondyloarthopathy," and insert -- spondyloarthropathy, --.

Column 28, Line 66, delete "thromboangitis" and insert -- thromboangiitis --.

Column 29, Line 4, delete "colitic" and insert -- colitis --.

Column 29, Line 10, delete "encephalitis/" and insert -- encephalomyelitis/ --.

Column 29, Line 11, delete "hemaphagocytic" and insert -- hemophagocytic --.

Column 29, Line 13, delete "Yersinia and Salmonella" and insert -- yersinia and salmonella --.

Column 29, Line 40, delete "a" and insert -- α --.

Column 30, Line 13 (approx.), delete "3-Amin omethyl" and insert -- 3-Aminomethyl --.

Column 30, Line 57, delete "O" and insert -- O— --.

Column 31, Line 1, delete "O" and insert -- O— --.

Column 31, Line 13 (approx.), delete "O" and insert -- O— --.

Column 31, Line 26, delete "O" and insert -- O— --.

Column 31, Line 56, delete "amino," and insert -- amino. --.

CERTIFICATE OF CORRECTION (continued)
U.S. Pat. No. 11,510,913 B1

In the Claims

Column 38, Line 33 (approx.), Claim 1, delete "bullosaother" and insert -- bullosa-other --.